(12) United States Patent
Gerster et al.

(10) Patent No.: US 8,258,217 B2
(45) Date of Patent: Sep. 4, 2012

(54) PERFLUOROALKYL SUBSTITUTED PHENOL DERIVATIVES AS SURFACE MODIFIERS

(75) Inventors: Michèle Gerster, Binningen (CH); Manuel Mihalic, Basel (CH)

(73) Assignee: BASF SE Ludwigshafen (DE)

( * ) Notice: Subject to any disclaimer, the term of this patent is extended or adjusted under 35 U.S.C. 154(b) by 603 days.

(21) Appl. No.: 12/310,259

(22) PCT Filed: Aug. 29, 2007

(86) PCT No.: PCT/EP2007/058954
§ 371 (c)(1),
(2), (4) Date: Feb. 18, 2009

(87) PCT Pub. No.: WO2008/028845
PCT Pub. Date: Mar. 13, 2008

(65) Prior Publication Data
US 2009/0242822 A1    Oct. 1, 2009

(30) Foreign Application Priority Data

Sep. 7, 2006 (EP) .................................. 06120278

(51) Int. Cl.
*C08K 5/136* (2006.01)
*C08K 5/375* (2006.01)

(52) U.S. Cl. ...... 524/171; 252/8.61; 252/8.62; 524/289; 524/330; 524/334; 524/341; 524/355; 524/368; 524/375

(58) Field of Classification Search .................. 524/330, 524/334, 341, 171, 289, 355, 368, 375; 252/8.61, 252/8.62
See application file for complete search history.

(56) References Cited

U.S. PATENT DOCUMENTS

| | | | | |
|---|---|---|---|---|
| 3,234,177 | A | * | 2/1966 | Van Schooten ............... 524/324 |
| 3,979,463 | A | * | 9/1976 | Endres ............................ 568/737 |
| 4,021,468 | A |  | 5/1977 | Lind ............................... 260/470 |
| 4,929,666 | A |  | 5/1990 | Schmidt et al. ............... 524/516 |
| 5,008,459 | A | * | 4/1991 | Meier et al. ..................... 568/46 |
| 5,310,773 | A | * | 5/1994 | Falk et al. ...................... 524/289 |
| 5,585,517 | A |  | 12/1996 | Deisenroth et al. ............ 562/583 |
| 5,663,273 | A |  | 9/1997 | Haniff et al. ................... 528/70 |
| 6,127,485 | A |  | 10/2000 | Klun et al. ..................... 525/199 |

FOREIGN PATENT DOCUMENTS

| | | | |
|---|---|---|---|
| EP | 0103211 | | 3/1984 |
| EP | 0190993 | | 8/1986 |
| EP | 0240601 | | 10/1987 |
| GB | 1396469 | | 6/1975 |
| JP | 50-003303 B | * | 2/1975 |
| WO | 02/38850 | | 5/2002 |
| WO | 02/055464 | | 7/2002 |

OTHER PUBLICATIONS

Meier, H., et al., "Reactions of Sulfur Containing Phenolic Antioxidants for Elastomers," Phosphorus, Sulfur and Silicon, 1999, vol. 153-154, pp. 275-300.*
English language abstract of EP 0240601, Oct. 14, 1987.
X. Cheng et al., J. Am. Chem. Soc., vol. 125, (2003), pp. 10977-10966.
M. Matsugi et al., J. Org. Chem., vol. 70, (2005), pp. 1636-1642.
R. Fraginals et al., J. Med. Chem., vol. 34, (1991), pp. 1024-1027.
X. H. Cheng et al., Angew. Chem. Int. Ed., vol. 41, No. 21, (2002), pp. 4031-4035.
S. Le Stang et al., Journal of Fluorine Chemistry, vol. 119, (2003), pp. 141-149.
L. Zhang et al., Journal of Fluorine Chemistry, vol. 102, (2000), pp. 55-59.
D. Bonafoux et al., Journal of Fluorine Chemistry, vol. 112, (2001), pp. 101-108.
X. Cheng et al., J. Am. Chem. Soc., vol. 126, (2004), pp. 12930-12940.

* cited by examiner

*Primary Examiner* — Vickey Nerangis
(74) *Attorney, Agent, or Firm* — Tyler A. Stevenson

(57) ABSTRACT

The instant invention relates to a composition comprising a) an organic material which is susceptible to oxidative, thermal or light-induced degradation, and b) at least one compound of the formula (I) wherein the general symbols are as defined in claim 1; especially wherein at least one of the radicals $R_2$, $R_3$ or $R_4$ is $-CH_2-CH(CH_3)-S(O)_p-R_{12}$, $-CH_2-CH_2-CH_2-S(O)_p-R_{12}$, $-CH_2-CH(R_{11})-CH_2-R_{12}$ or $-CH_2-CH=CH-R_{12}$, $R_{11}$ is hydrogen or halogen, $R_{12}$ is a monovalent perfluorinated alkyl or alkenyl, linear or branched organic radical having four to twenty fully fluorinated carbon atoms; or $-CH_2CH_2(CF_2)_mCF_3$, m is 3 to 12, and p is 0, 1 or 2. The compounds of the formula I are useful as reducers of surface energy for organic materials, for example synthetic polymer. Polymers with such a reduced surface energy possess an "easy-to-clean", "self-cleaning" "antisoiling", "soil-release" "antigraffiti", "oil resistance", "solvent resistance", "chemical resistance", "self lubricating", "scratch resistance", "low moisture absorption", "dirt pickup resistance", "slip properties" and "hydrophobic surface"; and anti-adhesion properties against proteins and against microorganism such as for example bacteria, fungi and algae.

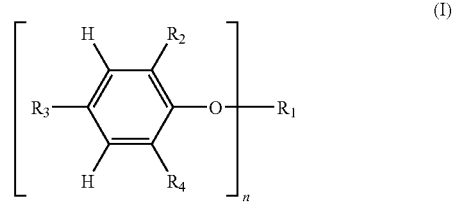

(I)

14 Claims, No Drawings

PERFLUOROALKYL SUBSTITUTED PHENOL DERIVATIVES AS SURFACE MODIFIERS

The present invention relates to compositions comprising an organic material, preferably a synthetic polymer, and at least a perfluoroalkyl substituted phenol derivative as reducer of surface energy of organic materials. Polymers with such a reduced surface energy possess an "easy-to-clean", "self-cleaning" "antisoiling" "soil-release", "antigraffiti", "oil resistance", "solvent resistance", "chemical resistance", "self lubricating", "scratch resistance", "low moisture absorption" "dirt pickup resistance", "slip properties" and "hydrophobic surface"; and anti-adhesion properties against proteins and against microorganism such as for example bacteria, fungi and algae.

The use of various fluorochemical compositions on fibers and fibrous substrates, such as for example textiles, carpets, paper, leather and non-woven webs to impart oil and water repellency is known for example in U.S. Pat. No. 6,127,485. This reference discloses hydrophobic and oleophobic fibers, films and molded articles comprising synthetic organic polymer wherein dispersed within the fiber, fabric or molded article and present at the surface of the fiber, fabric or molded article are fluorochemical compounds.

The known fluorochemicals do not satisfy in every respect the high requirements which a melt additive is required to meet as reducers of surface energy for organic materials, for example, for increasing the oil and water repellency of organic materials.

It has now been found that perfluoroalkyl substituted phenol derivatives are useful for various technical applications such as for example for increasing the oil and water repellency of organic materials like for example synthetic polymers. It has also now been found that perfluoroalkyl substituted phenol derivatives are useful for various technical applications such as for example the making of improved electret articles. In general, a electret is defined as a dielectric material, which exhibits an external electric field in the absence of an applied field [see also G. M. Sessler in Electrets; Sessler, G. M., Ed.; Laplacian Press: Morgan Hill, Calif., 1998; Vol. 1, Chapter 1].

The present invention therefore provides a composition comprising
a) an organic material which is susceptible to oxidative, thermal or light-induced degradation, and
b) at least one compound of the formula I

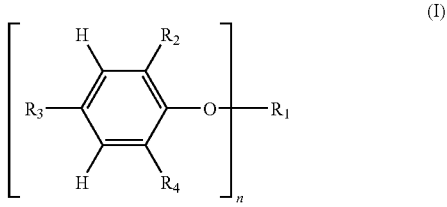

(I)

wherein, when n is 1,
$R_1$ is hydrogen, $C_1$-$C_{25}$alkyl, $C_2$-$C_{25}$alkenyl, —CO—$R_5$, —CH($R_{10}$)CO—$R_5$, —C($R_{10}$)$_2$CO—$R_5$, —CO—N($R_6$)—$R_7$, —CH($R_{10}$)CO—N($R_6$)—$R_7$, —C($R_{10}$)$_2$CO—N($R_6$)—$R_7$, —CH($R_{10}$)COO$R_5$ or —C($R_{10}$)$_2$CO—O$R_5$;
when n is 2,
$R_1$ is unsubstituted or with $C_1$-$C_4$alkyl, benzyl or phenyl substituted $C_1$-$C_{24}$alkylene; with oxygen or sulfur interrupted $C_2$-$C_{24}$alkylene; —CO—$R_8$—CO—, —CH($R_{10}$)CO—$R_8$—CO—CH($R_{10}$)—, —C($R_{10}$)$_2$CO—$R_8$—CO—C($R_{10}$)$_2$—, —CO—N($R_6$)—$R_9$—N($R_6$)—CO—, —CH($R_{10}$)CO—N($R_6$)—$R_9$—N($R_6$)—CO—CH($R_{10}$)—, —C($R_{10}$)$_2$CO—N ($R_6$)—$R_9$—N($R_6$)—CO—C($R_{10}$)$_2$—, —CH($R_{10}$)CO—O—$R_9$—O—CO—CH($R_{10}$)— or —C($R_{10}$)$_2$CO—O—$R_9$—O—CO—C($R_{10}$)$_2$—;
when n is 3,
$R_1$ is

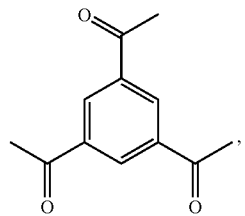

$R_2$, $R_3$ and $R_4$ independently of each other are hydrogen, $C_1$-$C_{25}$alkyl, $C_2$-$C_{25}$alkenyl, $C_1$-$C_{25}$alkoxy, —CH$_2$—CH (CH$_3$)—S(O)$_p$—$R_{12}$, —CH$_2$—CH$_2$—CH$_2$—S(O)$_p$—$R_{12}$, —CH$_2$—CH($R_{11}$)—CH$_2$—$R_{12}$, —CH$_2$—CH=CH—$R_{12}$,

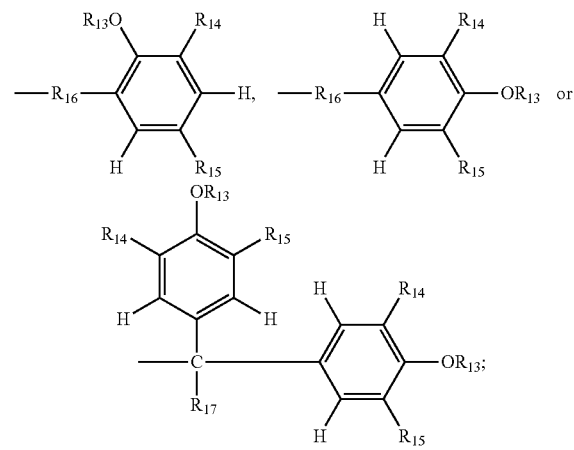

with the proviso that at least one of the radicals $R_2$, $R_3$ or $R_4$ is —CH$_2$—CH(CH$_3$)—S(O)$_p$—$R_{12}$, —CH$_2$—CH$_2$—CH$_2$—S(O)$_p$—$R_{12}$, —CH$_2$—CH($R_{11}$)—CH$_2$—$R_{12}$ or —CH$_2$—CH=CH—$R_{12}$;
$R_5$ is $C_1$-$C_{25}$alkyl, $C_2$-$C_{25}$alkenyl, unsubstituted or with $C_1$-$C_4$alkyl or halogen substituted phenyl; or $C_7$-$C_{12}$phenylalkyl,
$R_6$ is hydrogen or $C_1$-$C_4$alkyl,
$R_7$ is hydrogen, $C_1$-$C_{25}$alkyl, unsubstituted or with $C_1$-$C_4$alkyl or halogen substituted phenyl;
$R_8$ is phenylene, with nitro substituted phenylene; unsubstituted or with $C_1$-$C_4$alkyl, benzyl or phenyl substituted $C_1$-$C_{24}$alkylene; with oxygen or sulfur interrupted $C_2$-$C_{24}$alkylene;
$R_9$ is a direct bond; unsubstituted or with $C_1$-$C_4$alkyl, benzyl or phenyl substituted $C_2$-$C_{24}$alkylene; with oxygen or sulfur interrupted $C_2$-$C_{24}$alkylene; or

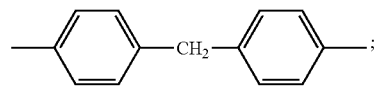

$R_{10}$ is hydrogen or $C_1$-$C_8$alkyl,
$R_{11}$ is hydrogen or halogen, $R_{12}$ is a monovalent perfluorinated alkyl or alkenyl, linear or branched organic radical having four to twenty fully fluorinated carbon atoms; or —$CH_2CH_2(CF_2)_mCF_3$, $R_{13}$ is hydrogen, $C_1$-$C_{25}$alkyl, $C_2$-$C_{25}$alkenyl, —CO—$R_5$, —CO—N($R_6$)—$R_7$ or —$CH_2$—CO—N($R_6$)—$R_7$, $R_{14}$ is hydrogen, $C_1$-$C_{25}$alkyl, $C_2$-$C_{25}$alkenyl, $C_1$-$C_{25}$alkoxy, —$CH_2$—CH($CH_3$)—S(O)$_p$—$R_{12}$, —$CH_2$—$CH_2$—$CH_2$—S(O)$_p$—$R_{12}$, —$CH_2$—CH($R_{11}$)—$CH_2$—$R_{12}$, or —$CH_2$—CH=CH—$R_{12}$, $R_{15}$ is hydrogen, $C_1$-$C_{25}$alkyl, $C_2$-$C_{25}$alkenyl, $C_1$-$C_{25}$alkoxy, —$CH_2$—CH($CH_3$)—S(O)$_p$—$R_{12}$, —$CH_2$—$CH_2$—$CH_2$—S(O)$_p$—$R_{12}$, —$CH_2$—CH($R_{11}$)—$CH_2$—$R_{12}$ or —$CH_2$—CH=CH—$R_{12}$, $R_{16}$ is unsubstituted or with $C_1$-$C_4$alkyl substituted methylene, —S—, —S(O)—, —S(O)$_2$— or —CO—;

$R_{17}$ is $C_1$-$C_4$alkyl, m is 3 to 12, n is 1, 2 or 3, and p is 0, 1 or 2.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

Alkenyl having 2 to 25 carbon atoms is a branched or unbranched radical such as, for example, propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl or n-4-octadecenyl.

Unsubstituted or with $C_1$-$C_4$alkyl, benzyl or phenyl substituted $C_1$-$C_{24}$alkylene is a branched or unbranched radical such as, for example methylene, ethylene, propylene, butylene, pentylene, hexylene, heptylene, octylene, nonylene, decylene, undecylene, dodecylene, tridecylene, tetradecylene, pentadecylene, hexadecylene, heptadecylene, octadecylene, methylmethylene, ethylmethylene, 2-methylpropylene, 2-phenylpropylene, 2-benzylpropylene, benzylmethylene or phenylmethylene (benzylidene).

$C_2$-$C_{24}$Alkylene interrupted by oxygen or sulfur is, for example, —$CH_2$—O—$CH_2$—, —$CH_2$—S—$CH_2$—, —$CH_2$—N($CH_3$)—$CH_2$—, —$CH_2$—O—$CH_2CH_2$—, —$CH_2CH_2$—O—$CH_2CH_2$—, —$CH_2CH_2$—O—$CH_2CH_2$—O—$CH_2CH_2$—(O—$CH_2CH_2$—)$_2$ O—$CH_2CH_2$—, —$CH_2CH_2$—(O—$CH_2CH_2$—)$_3$O—$CH_2CH_2$—, —$CH_2CH_2$—(O—$CH_2CH_2$—)$_4$O—$CH_2CH_2$— or —$CH_2CH_2$—S—$CH_2CH_2$—.

$C_1$-$C_4$Alkyl or halogen substituted phenyl which contains preferably from 1 to 3, especially 1 or 2, alkyl or halogen groups, is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl, 2,6-diethylphenyl, 2-chlorophenyl, 4-chlorophenyl or 2-methyl-4-chlorophenyl.

$C_7$-$C_{12}$Phenylalkyl unsubstituted or substituted on the phenyl radical by from 1 to 3 $C_1$-$C_4$alkyl groups is, for example, benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tertbutylbenzyl. Preference is given to benzyl.

The prefluoroalkyl moieties represent also mixtures of perfluoroalkyl moieties which means that $R_{12}$ usually concomitantly contains a small fraction of perfluoroalkyl groups with a lower number of carbon atoms and small fraction of perfluoroalkyl groups with a higher number of carbon atoms.

Alkoxy having up to 25 carbon atoms is a branched or unbranched radical, for example methoxy, ethoxy, propoxy, isopropoxy, n-butoxy, isobutoxy, pentyloxy, isopentyloxy, hexyloxy, heptyloxy, octyloxy, decyloxy, tetradecyloxy, hexadecyloxy or octadecyloxy.

Halogen is for example fluoro, chloro, bromo or iodo.

Of interest is a composition, wherein, when n is 1, $R_1$ is hydrogen, $C_1$-$C_{25}$alkyl, $C_2$-$C_{25}$alkenyl, —CO—$R_5$, —CH($R_{10}$)CO—$R_5$, —C($R_{10}$)$_2$CO—$R_5$, —CO—N($R_6$)—$R_7$, —CH($R_{10}$)CO—N($R_6$)—$R_7$, —C($R_{10}$)$_2$CO—N($R_6$)—$R_7$, —CH($R_{10}$)COO$R_5$ or —C($R_{10}$)$_2$CO—O$R_5$;

when n is 2, $R_1$ is unsubstituted or with $C_1$-$C_4$alkyl, benzyl or phenyl substituted $C_1$-$C_{24}$alkylene; with oxygen or sulfur interrupted $C_2$-$C_{24}$alkylene; —CO—$R_8$—CO—, —CH($R_{10}$)CO—$R_8$—CO—CH($R_{10}$)—, —C($R_{10}$)$_2$CO—$R_8$—CO—C($R_{10}$)$_2$—, —CO—N($R_6$)—$R_9$—N($R_6$)—CO—, —CH($R_{10}$)CO—N($R_6$)—$R_9$—N($R_6$)—CO—CH($R_{10}$)—, —C($R_{10}$)$_2$CO—N($R_6$)—$R_9$—N($R_6$)—CO—C($R_{10}$)$_2$—, —CH($R_{10}$)CO—O—$R_9$—O—CO—CH($R_{10}$)— or —C($R_{10}$)$_2$CO—O—$R_9$—O—CO—C($R_{10}$)$_2$—;

when n is 3, $R_1$ is

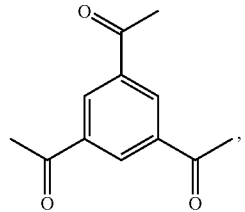

$R_2$, $R_3$ and $R_4$ independently of each other are hydrogen, $C_1$-$C_{25}$alkyl, $C_2$-$C_{25}$alkenyl, $C_1$-$C_{25}$alkoxy, —$CH_2$—CH($CH_3$)—S(O)$_p$—$R_{12}$, —$CH_2$—$CH_2$—$CH_2$—S(O)$_p$—$R_{12}$, —$CH_2$—CH($R_{11}$)—$CH_2$—$R_{12}$,

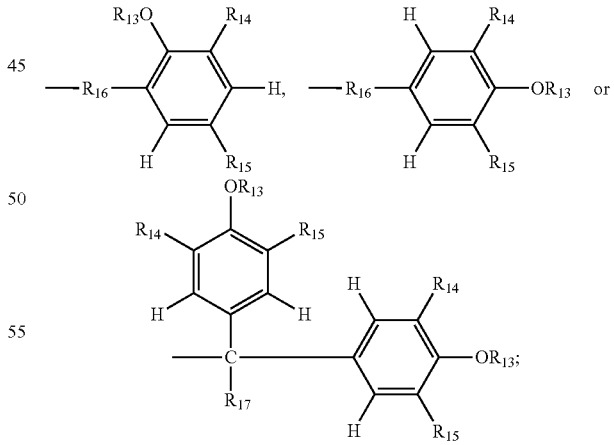

with the proviso that at least one of the radicals $R_2$, $R_3$ or $R_4$ is —$CH_2$—CH($CH_3$)—S(O)$_p$—$R_{12}$, —$CH_2$—$CH_2$—$CH_2$—S(O)$_p$—$R_{12}$ or —$CH_2$—CH($R_{11}$)—$CH_2$—$R_{12}$;

$R_5$ is $C_1$-$C_{25}$alkyl, $C_2$-$C_{25}$alkenyl, unsubstituted or with $C_1$-$C_4$alkyl or halogen substituted phenyl; or $C_7$-$C_{12}$phenylalkyl, $R_6$ is hydrogen or $C_1$-$C_4$alkyl, $R_7$ is hydrogen, $C_1$-$C_{25}$alkyl, unsubstituted or with $C_1$-$C_4$alkyl or halogen substituted phenyl;

$R_8$ is phenylene, with nitro substituted phenylene; unsubstituted or with $C_1$-$C_4$alkyl, benzyl or phenyl substituted $C_1$-$C_{24}$alkylene; with oxygen or sulfur interrupted $C_2$-$C_{24}$alkylene;

$R_9$ is a direct bond; unsubstituted or with $C_1$-$C_4$alkyl, benzyl or phenyl substituted $C_2$-$C_{24}$alkylene; with oxygen or sulfur interrupted $C_2$-$C_{24}$alkylene; or

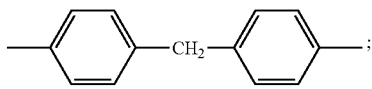

$R_{10}$ is hydrogen or $C_1$-$C_8$alkyl, $R_{11}$ is hydrogen or halogen, $R_{12}$ is a monovalent perfluorinated alkyl or alkenyl, linear or branched organic radical having four to twenty fully fluorinated carbon atoms, $R_{13}$ is hydrogen, $C_1$-$C_{25}$alkyl, $C_2$-$C_{25}$alkenyl, —CO—$R_5$, —CO—N($R_6$)—$R_7$ or —$CH_2$—CO—N($R_6$)—$R_7$, $R_{14}$ is hydrogen, $C_1$-$C_{25}$alkyl, $C_2$-$C_{25}$alkenyl, $C_1$-$C_{25}$alkoxy, —$CH_2$—CH($CH_3$)—S(O)$_p$—$R_{12}$, —$CH_2$—$CH_2$—$CH_2$—S(O)$_p$—$R_{12}$ or —$CH_2$—CH($R_{11}$)—$CH_2$—$R_{12}$, $R_{15}$ is hydrogen, $C_1$-$C_{25}$alkyl, $C_2$-$C_{25}$alkenyl, $C_1$-$C_{25}$alkoxy, —$CH_2$—CH($CH_3$)—S(O)$_p$—$R_{12}$, —$CH_2$—$CH_2$—$CH_2$—S(O)$_p$—$R_{12}$ or —$CH_2$—CH($R_{11}$)—$CH_2$—$R_{12}$, $R_{16}$ is unsubstituted or with $C_1$-$C_4$alkyl substituted methylene, —S—, —S(O)—, —S(O)$_2$— or —CO—

$R_{17}$ is $C_1$-$C_4$alkyl, n is 1, 2 or 3, and p is 0, 1 or 2.

Also of interest is a composition, wherein, when n is 1, $R_1$ is hydrogen, $C_1$-$C_{18}$alkyl, $C_2$-$C_{18}$alkenyl, —CO—$R_5$, —CO—N($R_6$)—$R_7$ or —$CH_2$—CO—N($R_6$)—$R_7$;

when n is 2, $R_1$ is unsubstituted or with $C_1$-$C_4$alkyl, benzyl or phenyl substituted $C_1$-$C_{18}$alkylene; with oxygen or sulfur interrupted $C_2$-$C_{18}$alkylene; —CO—$R_8$—CO—, —CO—N($R_6$)—$R_9$—N($R_6$)—CO— or —CH($R_{10}$)—CO—N($R_6$)—$R_9$—N($R_6$)—CO—CH($R_{10}$)—;

when n is 3, $R_1$ is

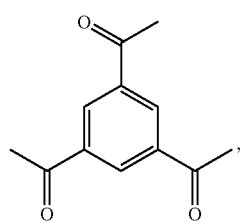

$R_2$, $R_3$ and $R_4$ independently of each other are hydrogen, $C_1$-$C_{18}$alkyl, $C_2$-$C_{18}$alkenyl, $C_1$-$C_{18}$alkoxy, —$CH_2$—CH($CH_3$)—S(O)$_p$—$R_{12}$, —$CH_2$—$CH_2$—$CH_2$—S(O)$_p$—$R_{12}$, —$CH_2$—CH($R_{11}$)—$CH_2$—$R_{12}$, —$CH_2$—CH=CH—$R_{12}$,

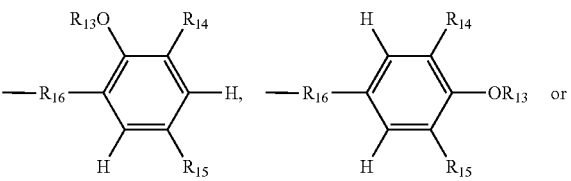

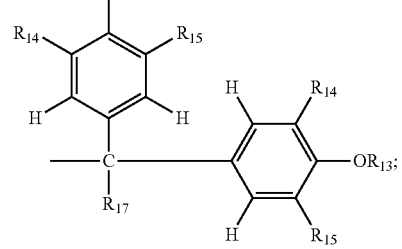

with the proviso that at least one of the radicals $R_2$, $R_3$ or $R_4$ is —$CH_2$—CH($CH_3$)—S(O)$_p$—$R_{12}$, —$CH_2$—$CH_2$—$CH_2$—S(O)$_p$—$R_{12}$, —$CH_2$—CH($R_{11}$)—$CH_2$—$R_{12}$ or —$CH_2$—CH=CH—$R_{12}$;

$R_5$ is $C_1$-$C_{18}$alkyl, $C_2$-$C_{18}$alkenyl, unsubstituted or with $C_1$-$C_4$alkyl or halogen substituted phenyl; or $C_7$-$C_{12}$phenylalkyl, $R_6$ is hydrogen or $C_1$-$C_4$alkyl, $R_7$ is hydrogen, $C_1$-$C_{18}$alkyl, unsubstituted or with $C_1$-$C_4$alkyl or halogen substituted phenyl;

$R_8$ is phenylene, unsubstituted or with $C_1$-$C_4$alkyl, benzyl or phenyl substituted $C_1$-$C_{24}$alkylene; with oxygen or sulfur interrupted $C_2$-$C_{24}$alkylene;

$R_9$ is a direct bond, unsubstituted or with $C_1$-$C_4$alkyl, benzyl or phenyl substituted $C_2$-$C_{18}$alkylene; or

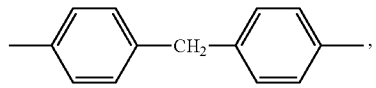

$R_{10}$ is hydrogen or $C_1$-$C_8$alkyl, $R_{11}$ is hydrogen or halogen, $R_{12}$ is a monovalent perfluorinated alkyl or alkenyl, linear or branched organic radical having four to twenty fully fluorinated carbon atoms, $R_{13}$ is hydrogen, $C_1$-$C_{18}$alkyl, $C_2$-$C_{18}$alkenyl, —CO—$R_5$, —CO—N($R_6$)—$R_7$ or —$CH_2$—CO—N($R_6$)—$R_7$, $R_{14}$ is hydrogen, $C_1$-$C_{18}$alkyl, $C_2$-$C_{18}$alkenyl, $C_1$-$C_{18}$alkoxy, —$CH_2$—CH($CH_3$)—S(O)$_p$—$R_{12}$, —$CH_2$—$CH_2$—$CH_2$—S(O)$_p$—$R_{12}$, —$CH_2$—CH($R_{11}$)—$CH_2$—$R_{12}$ or —$CH_2$—CH=CH—$R_{12}$, $R_{15}$ is hydrogen, $C_1$-$C_{18}$alkyl, $C_2$-$C_{18}$alkenyl, $C_1$-$C_{18}$alkoxy, —$CH_2$—CH($CH_3$)—S(O)$_p$—$R_{12}$, —$CH_2$—$CH_2$—$CH_2$—S(O)$_p$—$R_{12}$, —$CH_2$—CH($R_{11}$)—$CH_2$—$R_{12}$ or —$CH_2$—CH=CH—$R_{12}$, $R_{16}$ is unsubstituted or with $C_1$-$C_4$alkyl substituted methylene, —S—, —S(O)—, —S(O)$_2$— or —CO—

$R_{17}$ is $C_1$-$C_4$alkyl, n is 1, 2 or 3, and p is 0, 1 or 2.

Of very special interest is a composition wherein $R_{12}$ is saturated and contains 4-15 carbon atoms, is fully fluorinated and contains at least one terminal perfluoromethyl group; or —$CH_2CH_2(CF_2)_mCF_3$, and m is 3 to 12.

Of interest is a composition, wherein $R_2$, $R_3$ and $R_4$ independently of each other are hydrogen, $C_1$-$C_4$alkyl, $C_1$-$C_4$alkoxy, —$CH_2$—CH($CH_3$)—S(O)$_p$—$R_{12}$, —CH$_2$—CH$_2$—CH$_2$—S(O)$_p$—R$_{12}$, —CH$_2$—CH(R$_{11}$)—CH$_2$—R$_{12}$, —CH$_2$—CH=CH—R$_{12}$ or

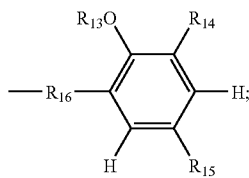

with the proviso that at least one of the radicals R$_2$, R$_3$ or R$_4$ is —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$ or —CH$_2$—CH=CH—R$_{12}$;

R$_{11}$ is hydrogen or halogen,

R$_{12}$ is a monovalent perfluorinated alkyl or alkenyl, linear or branched organic radical having four to twenty fully fluorinated carbon atoms, R$_{13}$ is hydrogen, C$_1$-C$_{18}$alkyl, C$_2$-C$_{18}$alkenyl or acetyl, R$_{14}$ is hydrogen, C$_1$-C$_{18}$alkyl, C$_2$-C$_{18}$alkenyl, C$_1$-C$_{18}$alkoxy, —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$ or —CH$_2$—CH=CH—R$_{12}$, R$_{15}$ is hydrogen, C$_1$-C$_{18}$alkyl, C$_2$-C$_{18}$alkenyl, C$_1$-C$_{18}$alkoxy, —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$ or —CH$_2$—CH=CH—R$_{12}$, R$_{16}$ is unsubstituted or with C$_1$-C$_4$alkyl substituted methylene, —S—, —S(O)—, —S(O)$_2$— or —CO and p is 0, 1 or 2.

Preferred is a composition, wherein, when n is 1,

R$_1$ is hydrogen, C$_1$-C$_{18}$alkyl, —CO—R$_5$, —CO—N(R$_6$)—R$_7$ or —CH$_2$—CO—N(R$_6$)—R$_7$;

when n is 2,

R$_1$ is unsubstituted or with C$_1$-C$_4$alkyl substituted C$_1$-C$_8$alkylene; —CO—R$_8$—CO—, —CO—N(R$_6$)—R$_9$—N(R$_6$)—CO— or —CH(R$_{10}$)—CO—N(R$_6$)—R$_9$—N(R$_6$)—CO—CH(R$_{10}$)—, when n is 3, R$_1$ is

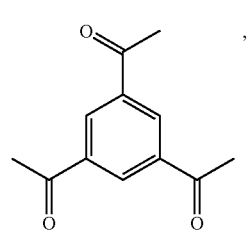

R$_2$, R$_3$ and R$_4$ independently of each other are hydrogen, C$_1$-C$_8$alkyl, C$_1$-C$_8$alkoxy, —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$, —CH$_2$—CH=CH—R$_{12}$

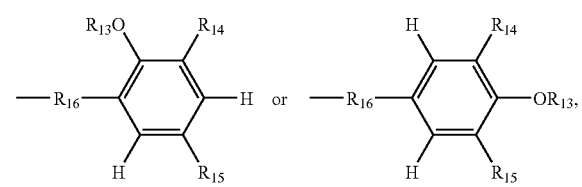

with the proviso that at least one of the radicals R$_2$, R$_3$ or R$_4$ is —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$ or —CH$_2$—CH=CH—R$_{12}$;

R$_5$ is C$_1$-C$_{18}$alkyl, unsubstituted or with C$_1$-C$_4$alkyl substituted phenyl; or C$_7$-C$_{12}$phenylalkyl, R$_6$ is hydrogen or C$_1$-C$_4$alkyl, R$_7$ is hydrogen, C$_1$-C$_8$alkyl, unsubstituted or with C$_1$-C$_4$alkyl substituted phenyl;

R$_8$ is phenylene, unsubstituted or with C$_1$-C$_4$alkyl substituted C$_1$-C$_{18}$alkylene;

R$_9$ is unsubstituted or with C$_1$-C$_4$alkyl substituted C$_2$-C$_{18}$alkylene; or

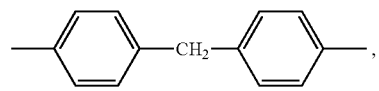

R$_{10}$ is hydrogen or C$_1$-C$_8$alkyl,

R$_{11}$ is hydrogen, fluoro, chloro or bromo,

R$_{12}$ is saturated and contains 4-15 carbon atoms, is fully fluorinated and contains at least one terminal perfluoromethyl group, R$_{13}$ is hydrogen, C$_1$-C$_{12}$alkyl, —CO—R$_5$, —CO—N(R$_6$)—R$_7$ or —CH$_2$—CO—N(R$_6$)—R$_7$, R$_{14}$ is hydrogen, C$_1$-C$_{12}$alkyl, C$_1$-C$_{12}$alkoxy, —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$ or —CH$_2$—CH=CH—R$_{12}$, R$_{15}$ is C$_1$-C$_{18}$alkyl, C$_1$-C$_{12}$alkoxy, —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$ or —CH$_2$—CH=CH—R$_{12}$, R$_{16}$ is unsubstituted or with C$_1$-C$_4$alkyl substituted methylene;

n is 1, 2 or 3, and p is 0.

Also preferred is a composition, wherein, when n is 1,

R$_1$ is hydrogen, C$_1$-C$_{18}$alkyl, —CO—R$_5$, —CO—N(R$_6$)—R$_7$ or —CH$_2$—CO—N(R$_6$)—R$_7$, when n is 2, R$_1$ is C$_1$-C$_8$alkylene, —CO—R$_8$—CO—, —CO—N(R$_6$)—R$_9$—N(R$_6$)—CO— or —CH(R$_{10}$)—CO—N(R$_6$)—R$_9$—N(R$_6$)—CO—CH(R$_{10}$)—, when n is 3, R$_1$ is

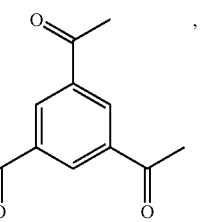

R$_2$, R$_3$ and R$_4$ independently of each other are hydrogen, C$_1$-C$_8$alkyl, C$_1$-C$_8$alkoxy, —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$, —CH$_2$—CH=CH—R$_{12}$,

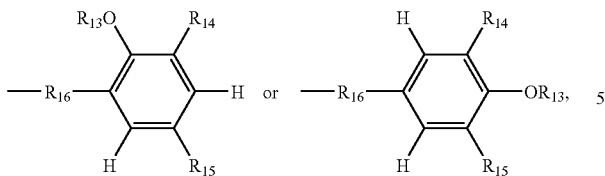

with the proviso that at least one of the radicals $R_2$, $R_3$ or $R_4$ is —$CH_2$—$CH(CH_3)$—$S(O)_p$—$R_{12}$, —$CH_2$—$CH_2$—$CH_2$—$S(O)_p$—$R_{12}$, —$CH_2$—$CH(R_{11})$—$CH_2$—$R_{12}$ or —$CH_2$—$CH$=$CH$—$R_{12}$;

$R_5$ is $C_1$-$C_{18}$alkyl, unsubstituted or with $C_1$-$C_4$alkyl substituted phenyl; or benzyl, $R_6$ is hydrogen, $R_7$ is hydrogen, $C_1$-$C_8$alkyl, unsubstituted or with $C_1$-$C_4$alkyl substituted phenyl;

$R_8$ is phenylene or $C_1$-$C_{18}$alkylene, $R_9$ is $C_2$-$C_{18}$alkylene or

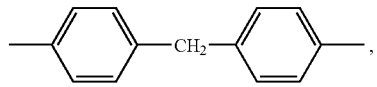

$R_{10}$ is $C_1$-$C_4$alkyl, $R_{11}$ is hydrogen or fluoro, choro or bromo, $R_{12}$ is —$(CF_2)_m CF_3$ or —$CH_2CH_2(CF_2)_m CF_3$, $R_{13}$ is hydrogen or —$CO$—$R_5$, $R_{14}$ is hydrogen or $C_1$-$C_8$alkyl or $C_1$-$C_8$alkoxy, $R_{15}$ is $C_1$-$C_4$alkyl, —$CH_2$—$CH(CH_3)$—$S(O)_p$—$R_{12}$, —$CH_2$—$CH_2$—$CH_2$—$S(O)_p$—$R_{12}$ or —$CH_2$—$CH(R_{11})$—$CH_2$—$R_{12}$, $R_{16}$ is methylene, m is 3 to 12, n is 1, 2 or 3, and p is 0.

Of very special interest is a composition, wherein, when n is 1, $R_1$ is hydrogen, $C_1$-$C_{12}$alkyl, —$CO$—$R_5$, —$CO$—$N(R_6)$—$R_7$ or —$CH_2$—$CO$—$N(R_6)$—$R_7$;

when n is 2, $R_1$ is methylene, —$CO$—$R_8$—$CO$— or —$CH(R_{10})$—$CO$—$N(R_6)$—$R_9$—$N(R_6)$—$CO$—$CH(R_{10})$—;

when n is 3, $R_1$ is

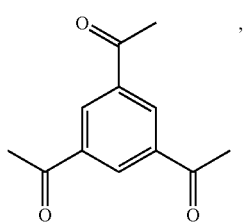

$R_2$, $R_3$ and $R_4$ independently of each other are hydrogen, $C_1$-$C_4$alkyl, $C_1$-$C_4$alkoxy, —$CH_2$—$CH(CH_3)$—$S(O)_p$—$R_{12}$, —$CH_2$—$CH_2$—$CH_2$—$S(O)_p$—$R_{12}$, —$CH_2$—$CH(R_{11})$—$CH_2$—$R_{12}$, —$CH_2$—$CH$=$CH$—$R_{12}$ or

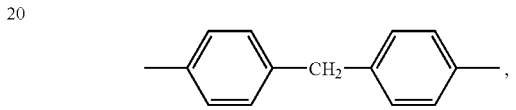

with the proviso that at least one of the radicals $R_2$, $R_3$ or $R_4$ is —$CH_2$—$CH(CH_3)$—$S(O)_p$—$R_{12}$, —$CH_2$—$CH_2$—$CH_2$—$S(O)_p$—$R_{12}$, —$CH_2$—$CH(R_{11})$—$CH_2$—$R_{12}$ or —$CH_2$—$CH$=$CH$—$R_{12}$;

$R_5$ is $C_1$-$C_{18}$alkyl, $R_6$ is hydrogen, $R_7$ is hydrogen, $C_1$-$C_6$alkyl, unsubstituted or with $C_1$-$C_4$alkyl substituted phenyl;

$R_8$ is phenylene or $$\underset{}{-\!\!\!\left\langle\!\!\!\bigcirc\!\!\!\right\rangle\!\!-CH_2-\!\!\!\left\langle\!\!\!\bigcirc\!\!\!\right\rangle\!\!-},$$

$R_9$ is ethylene, $R_{10}$ is methyl, $R_{11}$ is hydrogen, $R_{12}$ is —$(CF_2)_m CF_3$ or —$CH_2CH_2(CF_2)_m CF_3$, $R_{13}$ is hydrogen or acetyl, $R_{14}$ is $C_1$-$C_4$alkyl, $R_{15}$ is —$CH_2$—$CH(CH_3)$—$S(O)_p$—$R_{12}$, —$CH_2$—$CH_2$—$CH_2$—$S(O)_p$—$R_{12}$ or —$CH_2$—$CH(R_{11})$—$CH_2$—$R_{12}$, $R_{16}$ is methylene, m is 3 to 12, n is 1, 2 or 3, and p is 0.

The compounds of the formula I can be prepared by methods known in the art or in analogy to the process disclosed for example in U.S. Pat. No. 5,585,517 or Liebigs Ann. Chem. 1992, 209-216.

The compounds of the formula I are suitable as reducers of surface energy for organic materials. Polymers with such a reduced surface energy are suitable as oil and water repellency agents for organic materials and possess "easy-to-clean", "self-cleaning" "antisoiling", "soil-release", "anti-graffiti", "oil resistance", "solvent resistance", "chemical resistance", "self lubricating", "scratch resistance", "low moisture absorption", "dirt pickup resistance", "slip properties" and "hydrophobic surface"; and anti-adhesion properties against proteins and against microorganism such as for example bacteria, fungi and algae.

Illustrative examples of such materials are:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature.

b) catalytic polymerisation using a catalyst that normally contains one or more than one metal of groups Ivb, Vb, Vib or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copoyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends and alloys of the aforementioned polymers (polyblends), for example PP/EPDM, Polyamide/EPDM or ABS, PVC/EVA, PVC/ABS, PVC/MBS, PC/ABS, PC/Polyester, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The new compounds of the formula I can also be mixed or blended with one or more additives useful in polymer industry. The present invention relates therefore also to a mixture comprising ($\alpha$) a compound of the formula I, and ($\beta$) one or more additives selected from the group consisting of phenolic antioxidants, light-stabilizers, processing stabilizers, nucleating agent, biocides, antistatic agents, flame retardants and fillers.

Of special interest are mixtures wherein the weight ratio of the components ($\alpha$):($\beta$) is from 100:0.01 to 0.01 to 100.

Preferred organic materials are natural, semi-synthetic or, preferably, synthetic polymers.

Particularly preferred organic materials are synthetic polymers, most preferably thermoplastic polymers. Especially preferred organic materials are polyacetals, polyolefins such as polypropylene or polyethylene, polyether/polyurethanes, polyesters such as polybutylene terephthalate, polycarbonates or polyamides.

To be singled out for special mention is the efficacy of the compounds of the formula I as reducers of surface energy of the organic materials. Organic materials with low surface energy have intrinsically better properties like for example water and oil repellency, hydrophobicity, barrier properties, easy to clean, self cleaning, antigraffiti or solvent resistance.

The compounds of the formula I will preferably be added to the organic material in concentrations of 0.01 to 10%, preferably 0.1 to 2%, typically 0.1 to 2%, based on the weight of said material.

In addition to the compounds of the formula I, the composition of the invention may comprise further additives, such as for example the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl) phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2, 2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6. Alkylidenebisphenols, for example 2, 2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2, 6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra (5-tert-butyl-4-hydroxy-2-methylphenyl)pentane.

1.7. O-, N- and S-benzyl compounds, for example 3, 5,3', 5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl )amine, bis(4-tert-butyl-3-hydroxy-2,6-dimethylbenzyl)dithioterephthalate, bis(3,5-di-tert-butyl-4- hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3, 5,6-tetramethyl benzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4, 6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane; 3,9-bis [2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl )isocyanurate, N,N'-bis(hydroxyethyl)oxamide, 3-thiaundecanol, 3-thiapentadecanol, trimethylhexanediol, trimethylolpropane, 4-hydroxymethyl-1-phospha- 2,6,7-trioxabicyclo [2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis (hydroxyethyl)oxamide, 3-thiaundecanol, 3-thiapentadecanol, trimethylhexanediol, trimethylolpropane, 4-hydroxymethyl-1- phospha-2,6,7- trioxabicyclo [2.2.2]octane.

1.17. Amides of β-(3,5-di-tert-butyl-4-hydroxyphenyl) propionic acid e.g. N,N'-bis(3,5-di-tert-butyl-4-hydroxyphenyl propionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl] propionyloxy)ethyl]oxamide (Naugard® XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl) diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tertoctyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethyl benzyl)-2'-hydroxyphenyl) benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2- (3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

where R=3'-tert-butyl-4'-hydroxy-5'-2H-benzotriazol-2-ylphenyl, 2-[2'-hydroxy-3'-(α,α-dimethylbenzyl)-5'-(1,1,3, 3-tetramethylbutyl)phenyl]-benzotriazole; 2-[2'-hydroxy-3'-(1,1,3,3-tetramethylbutyl)-5'-(α,α-dimethylbenzyl)phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6, 6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethyl piperazinone), 4-benzoyl-2,2,6,6-tetramethylpiperidine, 4-stearyloxy-2,2,6, 6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7, 7,9,9-tetramethyl-1,3,8-triazaspiro[4.5]decane-2,4-dione, 3-dodecyl-1-(2,2,6,6-tetramethyl-4-piperidyl)pyrrolidine-2, 5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4, 6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2, 6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydrooxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4- [3-(2-ethylhexyl-1-oxy)-2-hydroxypropyloxy]phenyl}-4,6-bis(2,4-dimethylphenyl)-1,3,5-triazine, 2-[2-hydroxy-4-(2-ethylethoxy)phenyl]-4,6-diphenyl- 1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2, 4-di-tert-butylphenyl) phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N- dibenzylhydroxylamine, N,N- diethylhydroxylamine, N,N- dioctylhydroxylamine, N,N-dilaurylhydroxylamine, N,N-ditetradecylhydroxylamine, N,N-dihexadecylhydroxylamine, N,N-dioctadecyl hydroxylamine, N- hexadecyl-N-octadecyl hydroxyylamine, N-heptadecyl-N-octadecylhydroxylamine, N,N-dialkylhydroxylamine derived from hydrogenated tallow amine.

6. Nitrones, for example N-benzyl-alpha- phenylnitrone, N-ethyl-alpha-methylnitrone, N-octylalpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di (benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents blowing agents and infrared (IR) adsorbers.

Preferred IR absorbers are for example pigments, dyes or organometallic compounds. Examples of such pigments are for example disclosed in JP-A-2003221523. Examples of IR absorbing dyes are disclosed for example in JP-A-2003327865 or EP-A-1 306 404. IR absorbing organometallic compounds are for example disclosed in EP-A-1 266 931 or Chemical Abstract 117; 112529.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839; EP-A-0591102 or EP-A-1291384 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one or 3-(2-acetyl-5-isooctylphenyl)-5-isooctylbenzofuran-2-one.

The further additives are typically used in concentrations of 0.01 to 10%, based on the total weight of the material to be treated.

The novel compounds of the formula I can be used in particular together with phenolic antioxidants, light stabilizers and/or processing stabilizers.

Incorporation of component (b) and, if desired, further additives into the synthetic polymers is carried out by known methods, for example before or during compounding, extrusion, co-extrusion or else by applying the dissolved or dispersed compounds to the synthetic polymer, if appropriate with subsequent slow evaporation of the solvent.

The present invention also relates to a composition in the form of a masterbatch or concentrate comprising component (a) in an amount of from 5 to 90% and component (b) in an amount of from 5 to 80% by weight.

Component (b) and, if desired, further additives, can also be added before or during polymerisation or before crosslinking.

Component (b), with or without further additives, can be incorporated in pure form or encapsulated in waxes, oils or polymers into the synthetic polymer.

Component (b), with or without further additives, can also be sprayed onto the synthetic polymer. It is able to dilute other additives (for example the conventional additives indicated above) or their melts so that they too can be sprayed together with these additives onto the polymer. Addition by spraying on during the deactivation of the polymerization catalysts is particularly advantageous, it being possible to carry out spraying using, for example, the steam used for deactivation.

In the case of spherically polymerized polyolefins it may, for example, be advantageous to apply component (b), with or without other additives, by spraying.

The synthetic polymers prepared in this way can be employed in a wide variety of forms, for example as foams, films, fibres, tapes, moulding compositions, as profiles or as binders for coating materials, especially powder coatings, adhesives, putties or especially as thick-layer polyolefin mouldings which are in long-term contact with extractive media, such as, for example, pipes for liquids or gases, films, fibres, geomembranes, tapes, profiles or tanks.

The preferred thick-layer polyolefin mouldings have a layer thickness of from 1 to 50 mm, in particular from 1 to 30 mm, for example from 2 to 10 mm.

The compositions according to the invention can be advantageously used for the preparation of various shaped articles. Examples are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded or co-extruded plates, glazing for buildings (monolithic, twin or multiwall), aircraft, schools, extruded sheets, window film for architectural glazing, train, transportation, sanitary articles, and greenhouse.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

Of interest are compositions comprising as component (a) fibers and fabrics used in non-woven medical fabric and related apparel (surgical gowns, drapes, bandages), construction fabrics (house wrapping, roofing, swimming-pool wrapping) and home furnishing (carpets, table linens, shower curtains).

Of special interest are compositions comprising as component (a) fibers and nonwovens.

Thus, a further embodiment of the present invention relates to a shaped article, in particular a film, pipe, profile, bottle, tank or container, fiber containing a composition as described above.

A further embodiment of the present invention relates to a molded article containing a composition as described above. The molding is in particular effected by injection, blow, compression, roto-molding or slush-molding or extrusion.

The present invention also relates to a process for reducing the surface energy of organic materials which comprises treating the organic material with at least a compound of the formula I.

The preferred compounds of the formula I and optionally further additives, in the process for reducing the surface energy of organic materials are the same as those described for the composition.

A preferred embodiment of the present invention is also the use of a compound of the formula I as reducer of surface energy for organic materials.

Most of the compounds of the formula I are new. A further object of the invention are therefore also new compounds of the formula I

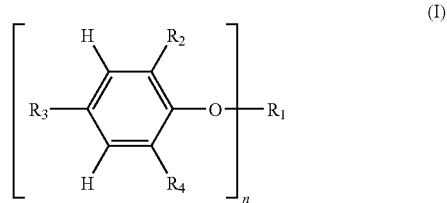

wherein, when n is 1,
$R_1$ is hydrogen, $C_1$-$C_{25}$alkyl, $C_2$-$C_{25}$alkenyl, —CO—$R_5$, —CH($R_{10}$)CO—$R_5$, —C($R_{10}$)$_2$CO—$R_5$, —CO—N($R_6$)—$R_7$, —CH($R_{10}$)CO—N($R_6$)—$R_7$, —C($R_{10}$)$_2$CO—N($R_6$)—$R_7$, —CH($R_{10}$)COO$R_5$ or —C($R_{10}$)$_2$CO—O$R_5$;
when n is 2,
$R_1$ is unsubstituted or with $C_1$-$C_4$alkyl, benzyl or phenyl substituted $C_1$-$C_{24}$alkylene; with oxygen or sulfur interrupted $C_2$-$C_{24}$alkylene; —CO—$R_8$—CO—, —CH($R_{10}$)CO—$R_8$—CO—CH($R_{10}$)—, —C($R_{10}$)$_2$CO—$R_8$—CO—C($R_{10}$)$_2$—, —CO—N($R_6$)—$R_9$—N($R_6$)—CO—, —CH($R_{10}$)CO—N($R_6$)—$R_9$—N($R_6$)—CO—CH($R_{10}$)—, —C($R_{10}$)$_2$CO—N($R_6$)—$R_9$—N($R_6$)—CO—C($R_{10}$)$_2$—, —CH($R_{10}$)CO—O—$R_9$—O—CO—CH($R_{10}$)— or —C($R_{10}$)$_2$CO—O—$R_9$—O—CO—C($R_{10}$)$_2$—;
when n is 3,
$R_1$ is

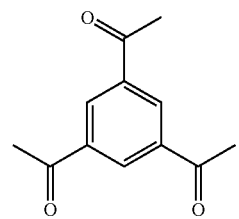

$R_2$, $R_3$ and $R_4$ independently of each other are hydrogen, $C_1$-$C_{25}$alkyl, $C_2$-$C_{25}$alkenyl, $C_1$-$C_{25}$alkoxy, —$CH_2$—CH($CH_3$)—$S(O)_p$—$R_{12}$, —$CH_2$—$CH_2$—$CH_2$—$S(O)_p$—$R_{12}$, —$CH_2$—$CH(R_{11})$—$CH_2$—$R_{12}$, —$CH_2$—CH=CH—$R_{12}$,

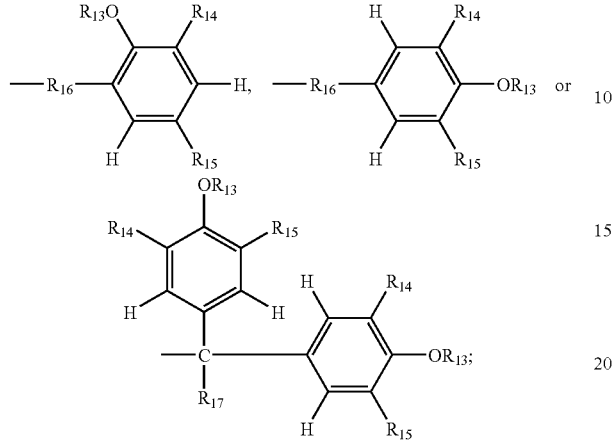

with the proviso that at least one of the radicals $R_2$, $R_3$ or $R_4$ is —$CH_2$—CH($CH_3$)—$S(O)_p$—$R_{12}$, —$CH_2$—$CH_2$—$CH_2$—$S(O)_p$—$R_{12}$, —$CH_2$—$CH(R_{11})$—$CH_2$—$R_{12}$ or —$CH_2$—CH=CH—$R_{12}$;

$R_5$ is $C_1$-$C_{25}$alkyl, $C_2$-$C_{25}$alkenyl, unsubstituted or with $C_1$-$C_4$alkyl or halogen substituted phenyl; or $C_7$-$C_{12}$phenylalkyl, $R_6$ is hydrogen or $C_1$-$C_4$alkyl, $R_7$ is hydrogen, $C_1$-$C_{25}$alkyl, unsubstituted or with $C_1$-$C_4$alkyl or halogen substituted phenyl;

$R_8$ is phenylene, with nitro substituted phenylene; unsubstituted or with $C_1$-$C_4$alkyl, benzyl or phenyl substituted $C_1$-$C_{24}$alkylene; with oxygen or sulfur interrupted $C_2$-$C_{24}$alkylene;

$R_9$ is a direct bond; unsubstituted or with $C_1$-$C_4$alkyl, benzyl or phenyl substituted $C_2$-$C_{24}$alkylene; with oxygen or sulfur interrupted $C_2$-$C_{24}$alkylene; or

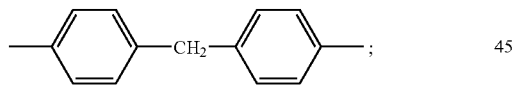

$R_{10}$ is hydrogen or $C_1$-$C_8$alkyl, $R_{11}$ is hydrogen or halogen, $R_{12}$ is a monovalent perfluorinated alkyl or alkenyl, linear or branched organic radical having four to twenty fully fluorinated carbon atoms; or —$CH_2CH_2(CF_2)_mCF_3$, $R_{13}$ is hydrogen, $C_1$-$C_{25}$alkyl, $C_2$-$C_{25}$alkenyl, —CO—$R_5$, —CO—$N(R_6)$—$R_7$ or —$CH_2$—CO—$N(R_6)$—$R_7$, $R_{14}$ is hydrogen, $C_1$-$C_{25}$alkyl, $C_2$-$C_{25}$alkenyl, $C_1$-$C_{25}$alkoxy, —$CH_2$—CH($CH_3$)—$S(O)_p$—$R_{12}$, —$CH_2$—$CH_2$—$CH_2$—$S(O)_p$—$R_{12}$, —$CH_2$—$CH(R_{11})$—$CH_2$—$R_{12}$, or —$CH_2$—CH=CH—$R_{12}$, $R_{15}$ is hydrogen, $C_1$-$C_{25}$alkyl, $C_2$-$C_{25}$alkenyl, $C_1$-$C_{25}$alkoxy, —$CH_2$—CH($CH_3$)—$S(O)_p$—$R_{12}$, —$CH_2$—$CH_2$—$CH_2$—$S(O)_p$—$R_{12}$, —$CH_2$—$CH(R_{11})$—$CH_2$—$R_{12}$ or —$CH_2$—CH=CH—$R_{12}$, $R_{16}$ is unsubstituted or with $C_1$-$C_4$alkyl substituted methylene, —S—, —S(O)—, —$S(O)_2$— or —CO—

$R_{17}$ is $C_1$-$C_4$alkyl, m is 3 to 12, n is 1, 2 or 3, and p is 0, 1 or 2; with the proviso that the compounds of the formulae I-9

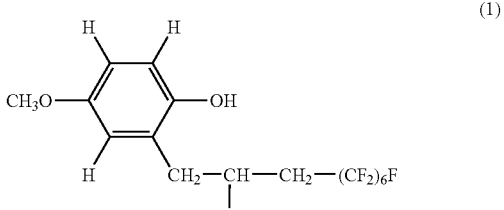

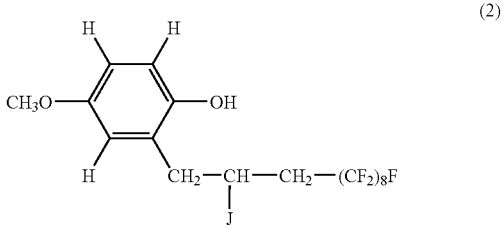

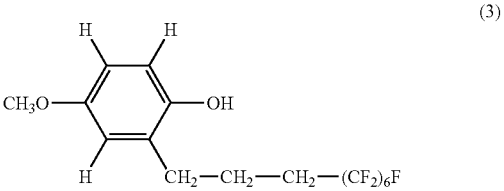

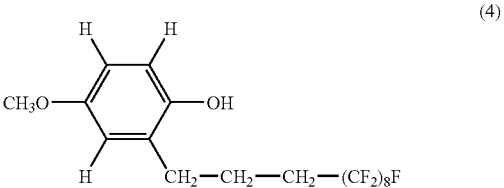

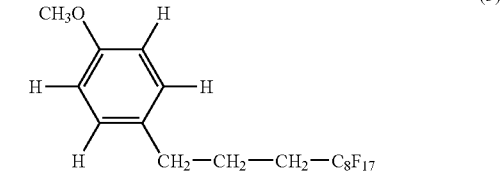

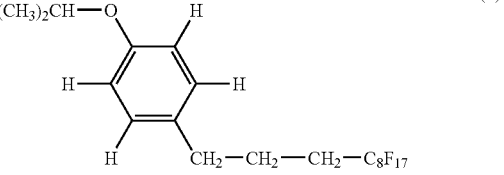

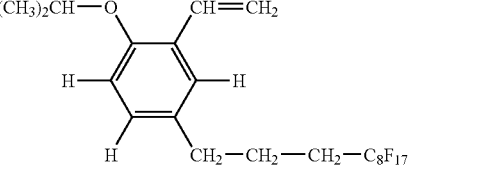

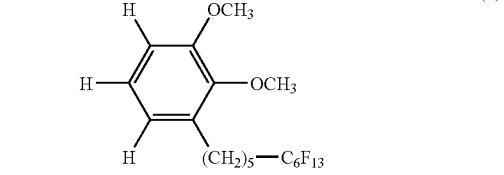

-continued

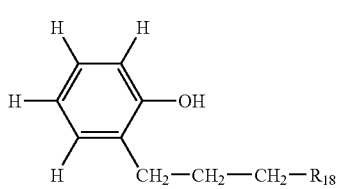

(9)

wherein $R_{18}$ is a monovalent perfluorinated alkyl, linear or branched organic radical having four to twenty fully fluorinated carbon atoms, are excluded.

The following examples illustrate the invention further. Parts or percentages relate to weight.

EXAMPLE 1

Preparation of Compound 101

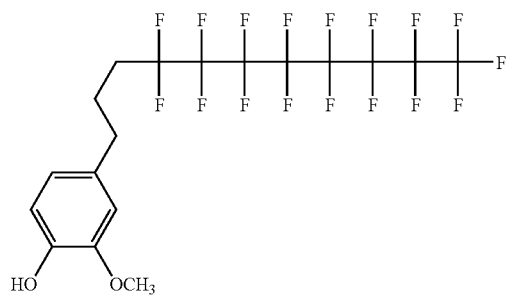

(101)

39.2 g (65.6 mmol) of the perfluoroalkyl iodide (Telomer-AN, from DuPont) with a homologue distribution and 10.8 g (65.6 mmol) of 4-allyl-2-methoxyphenol is suspended in 200 ml of dry 1,2-dichloroethane under nitrogen atmosphere. 0.50 g (3.3 mmol) of AIBN [2,2'-azo-bis-(2-methylbutyronitrile)] is then added and the reaction mixture is heated up to 80° C. and stirred for 12 hours. Each 2-3 hours, an additional quantity of AIBN (0.50 g) is added. The reaction mixture is cooled down under stirring. The precipitate is filtered, dried in an oven under vacuum to give 36.8 g of 4-(2-iodo-perfluoroalkyl)-2-methoxyphenol as a crude pale yellow, contaminated by residual amounts of unreacted 4-allyl-2-methoxyphenol and perfluoroalkyl iodide (Rfl).

The crude mass is then suspended in 300 ml of 1-propanol and 3.79 g (58.0 mmol) of activated Zn is added under nitrogen atmosphere. The reaction mixture is heated under reflux for 3 hours. After cooling to room temperature, cold aqueous HCl is added and the aqueous layer is extracted with ethyl acetate. The combined organic layers are washed several times with water, brine, dried over sodium sulfate, filtered and concentrated using a vacuum rotary evaporator to give 33.0 g of a waxy yellow solid. The crude product is purified by fractional distillation to give 28.0 g of the compound 101 as white solid, m.p. 77-78° C. $^1$H NMR: (300 MHz, CDCl$_3$): δ=6.92-6.82 (m, ArH, 1H); 6.85-6.72 (m, ArH, 2H); 3.92 (s, OCH$_3$, 3H); 2.66 (t, J=7.5 Hz, ArCH$_2$, 2H); 2.20-1.85 (m, CH$_2$CH$_2$CF$_2$+CH$_2$CH$_2$CF$_2$, 4H).

EXAMPLE 2

Preparation of Compound 102

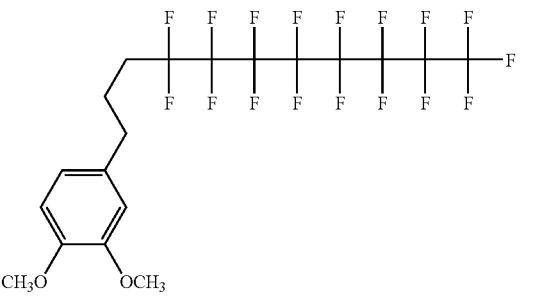

(102)

33.5 g (56.1 mmol) of the perfluoroalkyl iodide (Telomer-AN, from DuPont) with a homologue distribution and 10.0 g (56.1 mmol) of 4-allyl-1,2-dimethoxybenzene is suspended in 200 ml of dry 1,2-dichloroethane under nitrogen atmosphere. 0.46 g (2.8 mmol) of AIBN [2,2'-azo-bis-(2-methylbutyronitrile)] is then added and the reaction mixture is heated up to 80° C. and stirred for 24 hours. Each 2-3 hours, an additional quantity of AIBN (0.50 g). The reaction mixture is cooled down under stirring and the solvent is evaporated using a vacuum rotary evaporator to give a brown solid residue. The crude product is recrystallized from acetonitrile to afford 22.9 g of 4-(2-iodo-perfluoroalkyl)-1,2-dimethoxybenzene contaminated by residual amounts of unreacted 4-allyl-1,2-dimethoxybenzene and perfluoroalkyl iodide (Rfl).

4.0 g (5.15 mmol) of the crude mass is then suspended in 40 ml dry toluene. 42 mg (0.26 mmol) of AIBN [2,2'-azo-bis-(2-methylbutyronitrile)] and 1.54 g (5.15 mmol) of tributyltin hydride are added under nitrogen atmosphere. The reaction mixture is heated at 75° C. for 5 hours. After cooling to room temperature, the solvent is removed under reduced pressure. The solid residue is dissolved in methylene chloride and 50 ml of 1M NaOH is added. The reaction mixture is stirred vigorously for one hour. The organic layer is washed with brine, dried over sodium sulfate, filtered and concentrated using a vacuum rotary evaporator to give 3.60 g of a crude pale yellow solid. The crude material is purified by flash chromatography (hexane/ethyl acetate: 2:1) to give 1.80 g of the compound 102 as white solid, m.p. 69-73° C. $^1$H NMR: (300 MHz, CDCl$_3$): δ=6.90-6.80 (m, ArH, 1H); 6.80-6.65 (m, ArH, 2H); 3.91 (s, OCH₃, 3H); 3.89 (s, OCH₃, 3H); 2.68 (t, J=7.5 Hz, ArCH₂, 2H); 2.20-1.85 (m, CH₂CH₂CF₂+CH₂CH₂CF₂, 4H).

EXAMPLE 3

Preparation of a Compound 103

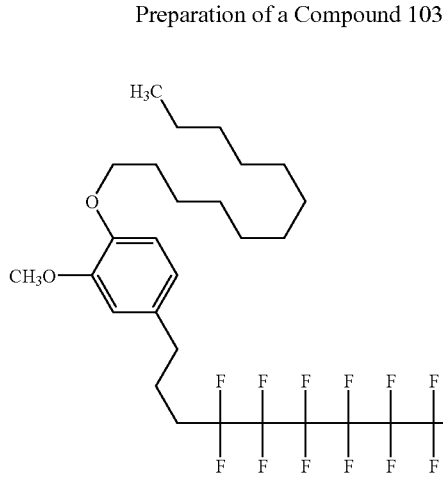

(103)

A mixture of 1.00 g (1.57 mmol) of compound 101 [prepared according to Example 1], 0.39 g (1.57 mmol) of 1-bromododecane and 0.43 g (3.14 g) of pulverized K₂CO₃ in 40 ml of dry acetone is heated under reflux for 2 days. The reaction mixture is poured into ethyl acetate, washed with 1N NH₄Cl, then with brine, dried over Na₂SO₄, filtered and concentrated using a vacuum rotary evaporator to give 1.30 g of an orange waxy solid. The crude material is purified by flash chromatography (hexane/ethyl acetate: 9:1) to give 0.80 g of a yellow wax contaminated by residual amounts of 1-bromodecane which are distilled off to afford 0.60 g of the compound 103, yellow wax. ¹H NMR: (300 MHz, CDCl₃): δ=6.88-6.78 (m, ArH, 1H); 6.75-6.65 (m, ArH, 2H); 4.01 (t, J=6.9 Hz, OCH₂, 2H); 3.89 (s, OCH₃, 3H); 2.67 (t, J=7.5 Hz, ArCH₂, 2H); 2.20-1.80 (m, CH₂CH₂CF₂+CH₂CH₂CF₂+CH₂, 6H); 1.55-1.15 (m, CH₂, 18H); 0.95-0.85 (m, CH₃, 3H).

EXAMPLE 4

Preparation of Compound 104

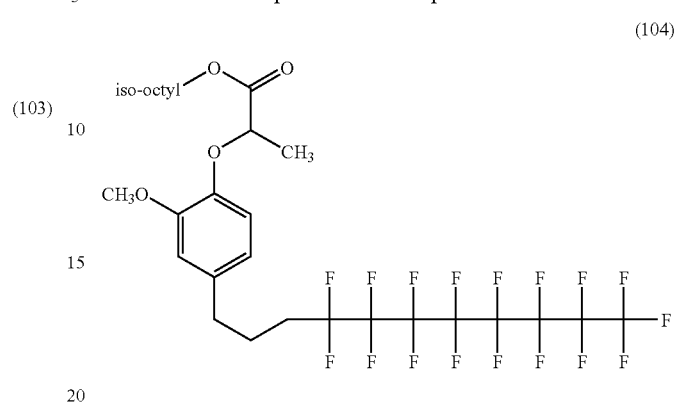

(104)

A mixture of 1.00 g (1.57 mmol) of compound 101 [prepared according to Example 1], 0.42 g (1.57 mmol) of isooctyl 2-bromopropionate (isooctyl mixture) and 0.43 g (3.14 g) of pulverized K₂CO₃ in 20 ml of dry methyl ethyl ketone is heated under reflux for 12 hours. The reaction mixture is poured into ethyl acetate, washed with 1N NH₄Cl, then with brine, dried over Na₂SO₄, filtered and concentrated using a vacuum rotary evaporator to give 1.05 g of a yellow oil. The crude material is purified by flash chromatography (hexane/ethyl acetate: 6:1) to give 0.80 g of the compound 104 as clear colourless oil. ¹H NMR: (300 MHz, CDCl₃): δ=6.85-6.60 (m, ArH, 3H); 4.74 (q, J=6.9 Hz, OCHCH₃, 1H); 4.30-4.00 (m, CO₂CH₂, 2H); 3.88 (s, OCH₃, 3H); 2.66 (t, J=7.5 Hz, ArCH₂, 2H); 2.20-1.80 (m, CH₂CH₂CF₂+CH₂CH₂CF₂, 4H); 1.75-0.70 (m, CH₂+CH₃, 18H).

EXAMPLE 5

Preparation of Compound 105

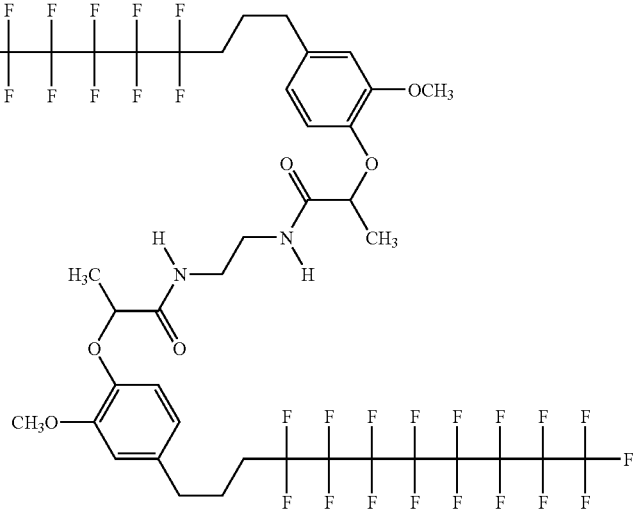

(105)

A mixture of 0.90 g (1.42 mmol) of compound 101 [prepared according to Example 1], 0.24 g (0.71 mmol) of 2-bromo-N-[2-(2-bromopropionylamino)ethyl]propionamide and 0.39 g (2.84 g) of pulverized $K_2CO_3$ in 30 ml of dry methyl ethyl ketone is heated under reflux for 2 days. The reaction mixture is poured into ethyl acetate, washed with 1N $NH_4Cl$, then with brine, dried over $Na_2SO_4$, filtered and concentrated using a vacuum rotary evaporator to give 0.90 g of a yellow waxy solid. The crude material is purified by flash chromatography (hexane/ethyl acetate: 1:3) to give 0.50 g of the compound 105 as white solid, m.p. 97-110° C. $^1$H NMR: (300 MHz, acetone-$d_6$): δ=7.75-7.55 (br s, NH, 2H); 7.05-6.90 (m, ArH, 4H); 6.85-6.70 (m, ArH, 2H); 4.60-4.40 (m, OCHCH$_3$, 2H); 3.95-3.80 (m, OCH$_3$, 6H); 3.50-3.30 (m, NHCH$_2$, 4H); 2.72 (t, J=7.5 Hz, ArCH$_2$, 4H); 2.40-2.15 (m, CH$_2$CH$_2$CF$_2$, 4H); 2.10-1.80 (m, CH$_2$CH$_2$CF$_2$, 4H); 1.55-1.40 (m, CH$_3$, 6H).

EXAMPLE 6

Preparation of Compound 106

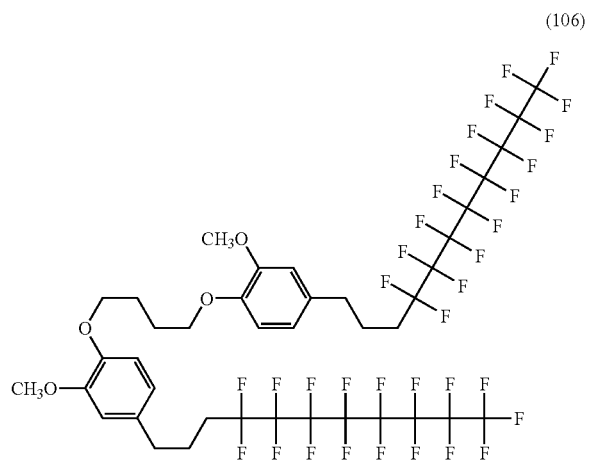

(106)

A mixture of 1.20 g (1.57 mmol) of compound 101 [prepared according to Example 1], 0.17 g (0.78 g) of 1,4-dibromobutane and 0.87 g (6.30 g) of pulverized $K_2CO_3$ in 40 ml of dry acetone is heated under reflux for 12 hours. The reaction mixture is poured into ethyl acetate and washed with water. The solid suspended in the organic phase is filtered, washed with tetrahydrofuran, dried in an oven to give 0.35 g of the compound 106 as white solid, m.p. 106-109° C. $^1$H NMR: (300 MHz, CDCl$_3$): δ=6.90-6.80 (m, ArH, 2H); 6.75-6.65 (m, ArH, 4H); 4.10 (t, J=5.7 Hz, OCH$_2$, 4H); 3.87 (s, OCH$_3$, 6H); 2.67 (t, J=7.5 Hz, ArCH$_2$, 4H); 2.20-1.85 (m, CH$_2$CH$_2$CF$_2$+CH$_2$CH$_2$CF$_2$+OCH$_2$CH$_2$, 12H).

EXAMPLE 7

Preparation of Compound 107

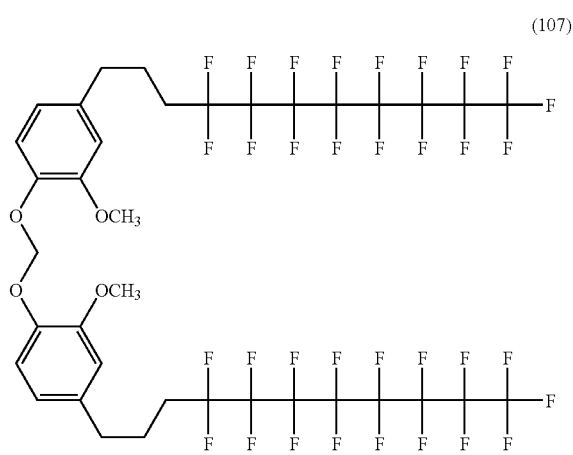

(107)

0.32 g (7.86 mmol) of pulverized sodium hydroxide is added at 40° C. to a mixture of 2.00 g (3.14 mmol) of compound 101 [prepared according to Example 1] and 3.20 g (37.7 mmol) of dichloromethane suspended in 9.0 ml of N-methylpyrrolidinone. The reaction mixture is heated at 60° C. for 7 hours. The reaction mixture is poured into ethyl acetate and washed with water. The organic phase is dried over Na$_2$SO$_4$, filtered and concentrated using a vacuum rotary evaporator to give 4.80 g of a yellow oil, still containing a large amount of the solvent N-methylpyrrolidinone. The crude material is purified by recrystallization from 40 ml of 2-propanol to give 0.80 g of the compound 107 as pale yellow solid, m.p. 58-64° C. $^1$H NMR: (300 MHz, acetone-$d_6$): δ=7.20-7.10 (m, ArH, 2H); 7.00-6.90 (m, ArH, 2H); 6.85-6.75 (m, ArH, 2H); 5.69 (s, OCH$_2$O, 2H); 3.90-3.85 (m, OCH$_3$, 6H); 2.75 (t, J=7.5 Hz, ArCH$_2$, 4H); 2.40-2.15 (m, CH$_2$CH$_2$CF$_2$, 4H); 2.10-1.80 (m, CH$_2$CH$_2$CF$_2$, 4H).

EXAMPLE 8

Preparation of Compound 108

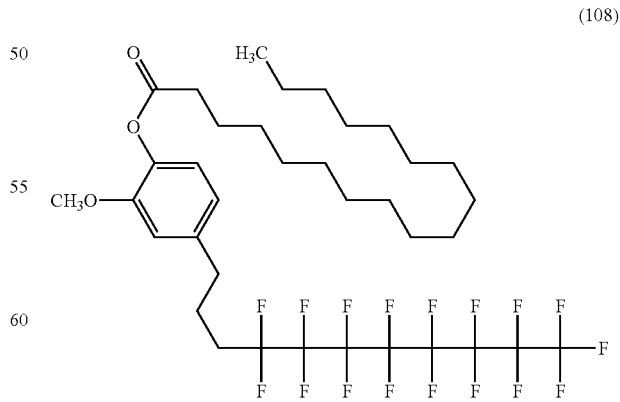

(108)

0.80 g (1.26 mmol) of compound 101 [prepared according to Example 1] and 0.15 g (1.31 mmol) of triethylamine are dissolved in 20 ml of tetrahydrofuran. 0.38 g (1.26 mmol) of stearoyl chloride is added to the reaction mixture at room temperature under nitrogen atmosphere. The reaction mixture is stirred at room temperature for 12 hours. Ethyl acetate (80 ml) is added and the organic phase is washed repeatedly with water until pH neutral. The organic phase is dried over magnesium sulfate, filtered and concentrated using a vacuum rotary evaporator to give 1.30 g of a pale yellow waxy solid. The crude product is purified by flash chromatography (hexane/ethyl acetate: 9:1) to give 0.95 g of the compound 108 as white solid, m.p. 53-56° C. $^1$H NMR: (300 MHz, CDCl$_3$): δ=7.00-6.90 (m, ArH, 1H); 6.80-6.70 (m, ArH, 2H); 3.84 (s, OCH$_3$, 3H); 2.72 (t, J=7.5 Hz, ArCH$_2$, 2H); 2.59 (t, J=7.5 Hz, CH$_2$CO$_2$, 2H); 2.20-1.90 (m, CH$_2$CH$_2$CF$_2$+CH$_2$CH$_2$CF$_2$, 4H); 1.85-1.70 (m, CH$_2$CH$_2$CO$_2$, 2H); 1.50-1.20 (m, CH$_2$, 28H); 0.95-0.85 (m, CH$_3$, 3H).

EXAMPLE 9

Preparation of Compound 109

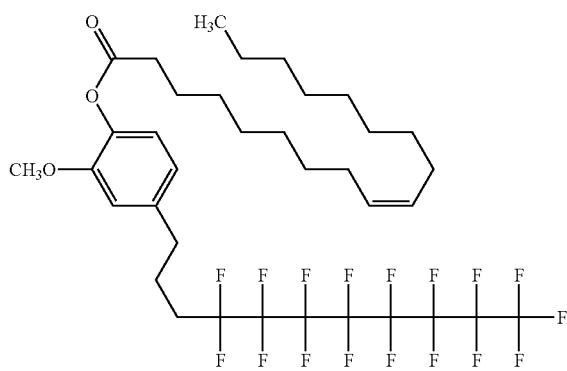
(109)

1.00 g (1.57 mmol) of compound 101 [prepared according to Example 1] and 0.19 g (1.88 mmol) of triethylamine are dissolved in 20 ml of tetrahydrofuran. 0.56 g (1.57 mmol) of oleoyl chloride (85%) is added to the reaction mixture at room temperature under nitrogen atmosphere. The reaction mixture is stirred at room temperature for 12 hours. Ethyl acetate (80 ml) is added and the organic phase is washed repeatedly with water until pH neutral. The organic phase is dried over magnesium sulfate, filtered and concentrated using a vacuum rotary evaporator to give 1.40 g of a yellow wax. The crude product is purified by flash chromatography (hexane/ethyl acetate: 6:1) to give 1.15 g of the compound 109 as pale yellow wax. $^1$H NMR: (300 MHz, CDCl$_3$): δ=7.00-6.90 (m, ArH, 1H); 6.85-6.70 (m, ArH, 2H); 5.45-5.30 (m, CH=CH, 2H); 3.85 (s, OCH$_3$, 3H); 2.72 (t, J=7.5 Hz, ArCH$_2$, 2H); 2.59 (t, J=7.5 Hz, CH$_2$CO$_2$, 2H); 2.25-1.85 (m, CH$_2$CH$_2$CF$_2$+CH$_2$CH$_2$CF$_2$+CH$_2$CH=CHCH$_2$, 8H); 1.85-1.70 (m, CH$_2$CH$_2$CO$_2$, 2H); 1.50-1.20 (m, CH$_2$, 20H); 0.95-0.80 (m, CH$_3$, 3H).

EXAMPLE 10

Preparation of Compound 110

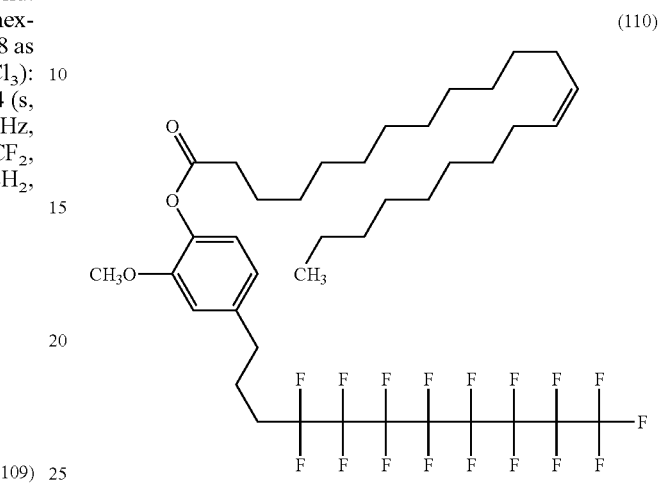
(110)

1.09 g (1.71 mmol) of x (example 1) and 0.21 g (2.05 mmol) of triethylamine are dissolved in 10 ml of tetrahydrofuran. 0.61 g (1.71 mmol) of erucoyl chloride dissolved in 10 ml of tetrahydrofuran is added to the reaction mixture at room temperature under nitrogen atmosphere. The reaction mixture is stirred at room temperature for 12 hours. Ethyl acetate (80 ml) is added and the organic phase is washed repeatedly with water until pH neutral. The organic phase is dried over magnesium sulfate, filtered and concentrated using a vacuum rotary evaporator to give 2.00 g of a brown wax. The crude product is purified by flash chromatography (hexane/ethyl acetate: 15:1) to give 0.60 g of the compound 110 as yellow wax. Its spectroscopic properties are in agreement with compound 110.

EXAMPLE 11

Preparation of Compound 111

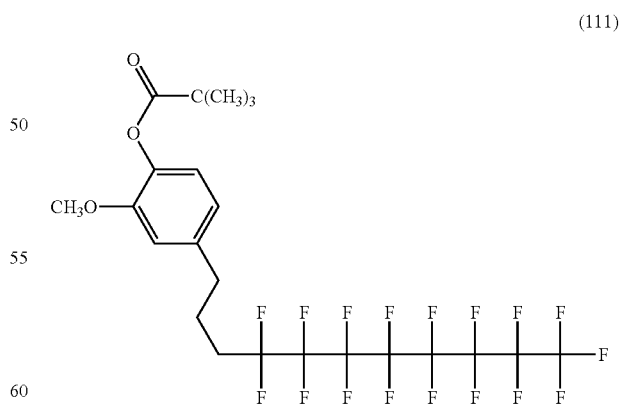
(111)

1.50 g (2.36 mmol) of compound 101 [prepared according to Example 1] and 0.29 g (2.83 mmol) of triethylamine are dissolved in 20 ml of tetrahydrofuran. 0.28 g (2.36 mmol) of pivaloyl chloride is added to the reaction mixture at room temperature under nitrogen atmosphere. The reaction mixture is stirred at room temperature for 18 hours. Ethyl acetate (80 ml) is added and the organic phase is washed repeatedly with water until pH neutral. The organic phase is dried over magnesium sulfate, filtered and concentrated using a vacuum rotary evaporator to give 1.70 g of a colourless wax. The crude product is purified by flash chromatography (hexane/ethyl acetate: 15:1) to give 1.50 g of the compound III as white solid, m.p. 56-68° C. $^1$H NMR: (300 MHz, CDCl$_3$): δ=7.00-6.90 (m, ArH, 1H); 6.80-6.70 (m, ArH, 2H); 3.82 (s, OCH$_3$, 3H); 2.72 (t, J=7.5 Hz, ArCH$_2$, 2H); 2.20-1.90 (m, CH$_2$CH$_2$CF$_2$+CH$_2$CH$_2$CF$_2$, 4H); 1.38 (s, tert-butyl, 9H).

EXAMPLE 12

Preparation of Compound 112

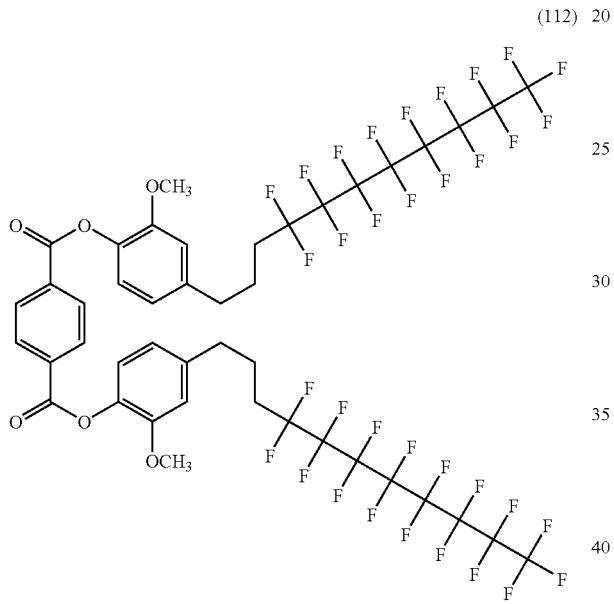

(112)

1.50 g (2.36 mmol) of compound 101 [prepared according to Example 1] and 0.29 g (2.83 mmol) of triethylamine are dissolved in 20 ml of tetrahydrofuran. 0.24 g (1.18 mmol) of terephthaloyl chloride is added to the reaction mixture at room temperature under nitrogen atmosphere. The reaction mixture is stirred at room temperature for 12 hours. The reaction mixture is poured into ethyl acetate and washed with water. The solid suspended in the organic phase is filtered, washed with tetrahydrofuran, dried in an oven to give 0.30 g of a white solid. The organic layer is washed with water, dried over magnesium sulfate, filtered and concentrated using a vacuum rotary evaporator to give 0.70 g of a white solid. The combined solids are purified by recrystallization from ethyl acetate to give 0.55 g of the compound 112 as white solid, m.p. 160-244° C. $^1$H NMR: (300 MHz, acetone-d$_6$): δ=8.37 (s, ArH, 4H); 7.22-7.12 (m, ArH, 4H); 7.00-6.90 (m, ArH, 2H); 3.85 (s, OCH$_3$, 6H); 2.90-2.80 (m, ArCH$_2$, 4H); 2.50-2.20 (m, CH$_2$CH$_2$CF$_2$, 4H); 2.10-1.95 (m, CH$_2$CH$_2$CF$_2$, 4H).

EXAMPLE 13

Preparation of Compound 113

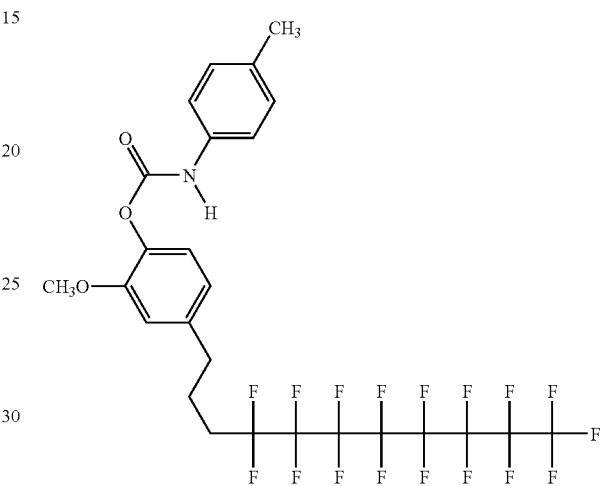

(113)

1.00 g (1.57 mmol) of compound 101 [prepared according to Example 1] and 0.02 g (0.16 mmol) of triethylamine are dissolved in 15 ml of dry tetrahydrofuran. 0.21 g (1.57 mmol) of p-tolylisocyanate is added to the reaction mixture at room temperature under nitrogen atmosphere. The reaction mixture is stirred at room temperature for 12 hours. Ethyl acetate is added and the organic phase is washed repeatedly with water and brine until pH neutral. The organic phase is dried over magnesium sulfate, filtered and concentrated using a vacuum rotary evaporator to give 1.30 g of a white solid. The crude product is purified by flash chromatography (hexane/ethyl acetate: 5:1) to give 1.10 g of the compound 113 as white solid, m.p. 102-135° C. $^1$H NMR: (300 MHz, CDCl$_3$): δ=7.40-7.25 (m, ArH, 2H); 7.20-7.10 (m, ArH, 3H); 7.00-6.85 (br s, NH, 1H); 6.85-6.75 (m, ArH, 2H); 3.87 (s, OCH$_3$, 6H); 2.73 (t, J=7.5 Hz, ArCH$_2$, 2H); 2.34 (s, CH$_3$, 3H); 2.25-1.90 (m, CH$_2$CH$_2$CF$_2$+CH$_2$CH$_2$CF$_2$, 4H).

EXAMPLE 14

Preparation of Compound 114

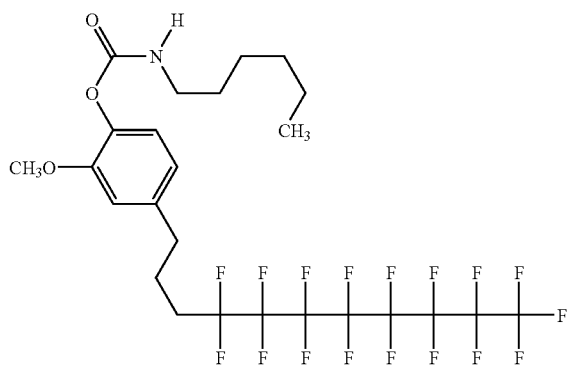

(114)

0.02 g (0.18 mmol) of 1,4-diaza-bicyclo[2.2.2]octane (DABCO) is added at room temperature to a mixture of 1.12 g (1.76 mmol) of compound 101 [prepared according to Example 1] and 0.28 g (2.11 mmol) of hexylisocyanate dissolved in 20 ml of dry dioxane. The reaction mixture is stirred at 45° C. for 2 days. Ethyl acetate is added and the organic phase is washed repeatedly with water and brine until pH neutral. The organic phase is dried over magnesium sulfate, filtered and concentrated using a vacuum rotary evaporator to give 1.40 g of a yellow wax. The crude product is purified flash chromatography (hexane/ethyl acetate: 6:1) to give 0.75 g of the compound 114 as white waxy solid. $^1$H NMR: (300 MHz, CDCl$_3$): δ=7.10-7.00 (m, ArH, 1H); 6.80-6.70 (m, ArH, 2H); 5.10-5.00 (br s, NH, 1H); 3.86 (s, OCH$_3$, 3H); 3.35-3.20 (m, NHCH$_2$, 2H); 2.71 (t, J=7.5 Hz, ArCH$_2$, 2H); 2.34 (s, CH$_3$, 3H); 2.20-1.85 (m, CH$_2$CH$_2$CF$_2$+CH$_2$CH$_2$CF$_2$, 4H); 1.65-1.50 (m, NHCH$_2$CH$_2$, 2H); 1.45-1.20 (m, CH$_2$, 6H); 1.00-0.85 (m, CH$_3$, 3H).

EXAMPLE 15

Preparation of Compound 115

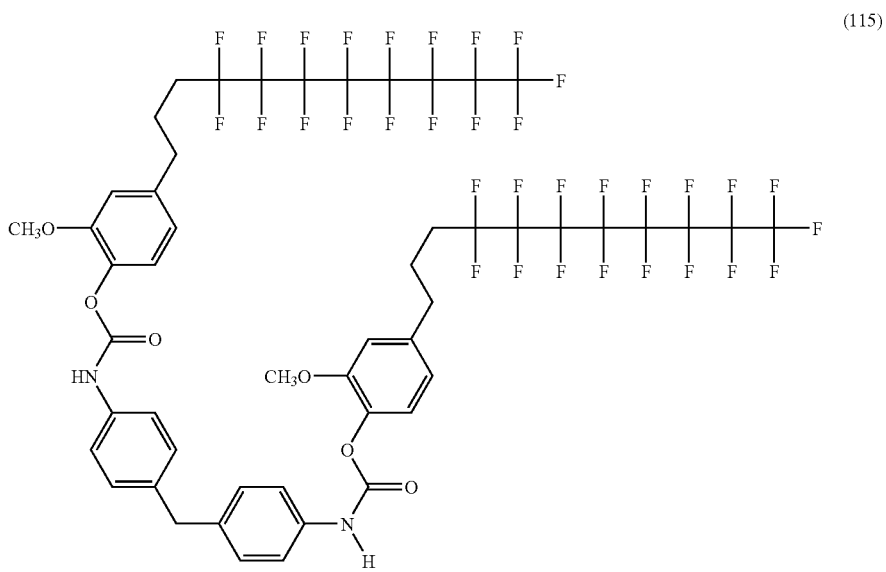

(115)

1.25 g (1.97 mmol) of compound 101 [prepared according to Example 1] and 0.24 g (2.37 mmol) of triethylamine are dissolved in 100 ml of dry tetrahydrofuran. 0.25 g (1.00 mmol) of 4,4'-methylene-bisphenylisocyanate is added to the reaction mixture at room temperature under nitrogen atmosphere. The reaction mixture is stirred at room temperature for 12 hours. Ethyl acetate is added and the organic phase is washed repeatedly with water and brine until pH neutral. The organic phase is dried over magnesium sulfate, filtered and concentrated using a vacuum rotary evaporator to give 1.70 g of a pale yellow solid. The crude product is purified by recrystallization in acetone to give 0.50 g of the compound 115 as white solid, m.p. 177-183° C. $^1$H NMR: (300 MHz, CDCl$_3$): δ=7.45-7.35 (m, ArH, 4H); 7.20-7.05 (m, ArH, 6H); 7.05-6.85 (br s, NH, 2H); 6.85-6.75 (m, ArH, 4H); 3.93 (s, ArCH$_2$Ar, 2H); 3.86 (s, OCH$_3$, 6H); 2.73 (t, J=7.5 Hz, ArCH$_2$, 4H); 2.25-1.85 (m, CH$_2$CH$_2$CF$_2$+CH$_2$CH$_2$CF$_2$, 8H).

EXAMPLE 16

Preparation of a Mixture of Compounds 116A and 116B

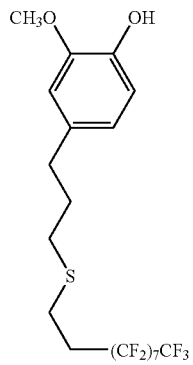

(116A)

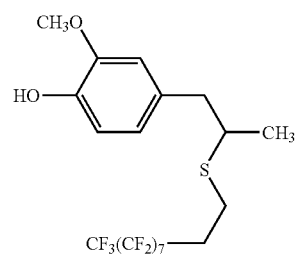

(116B)

A mixture of 6.40 g (38.7 mmol) of 4-allyl-2-methoxyphenol, 18.6 g (38.7 mmol) of 1H,1H,2H,2H-perfluorodecane-1-thiol and 0.32 g (1.94 mmol) of AIBN [2,2'-azo-bis-(2-methylbutyronitrile)] in 50 ml of dry toluene is heated at 80° C. for 2 days. Each 2-3 hours, an additional quantity of AIBN (0.32 g) is added. The reaction mixture is evaporated to dryness to give 27.3 g of a white wax. The crude material is purified by distillation (175° C./0.05 mbar) to give 14.7 g of a mixture of regioisomers 116A and 116B (GC: appr. 80%/20%) as white solid, m.p. 65-67° C. $^1$H NMR: (300 MHz, CDCl$_3$): major regioisomer 116A: δ=6.95-6.80 (m, ArH, 1H); 6.75-6.65 (m, ArH, 2H); 5.49 (s, OH, 1H); 3.90 (s, OCH$_3$, 3H); 2.80-2.50 (m, ArCH$_2$CH$_2$CH$_2$SCH$_2$, 6H); 2.50-2.20 (m, SCH$_2$CH$_2$CF$_2$, 2H); 2.00-1.85 (m, ArCH$_2$CH$_2$, 2H). Significant peaks of the minor isomer 116B: 5.53 (s, OH, 1H); 3.05-2.80 (m, 2H); 1.28 (d, J=6.6 Hz, CH$_3$, 3H). $^{13}$C-NMR (100 MHz, CDCl$_3$): 146.46; 144.32; 143.89; 133.06; 130.93; 121.92; 121.00; 114.28; 111.62; 110.92; 55.80; 43.36; 42.20 (minor); 34.30; 32.30; 32.08; 31.86; 31.41; 31.06; 22.53; 21.22; 20.71 (minor).

HPLC-UV/APCI-MS: [M-1]$^+$=644.07

EXAMPLE 17

Preparation of a Mixture of Compounds 117A and 117B

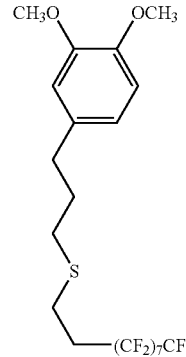

(117A)

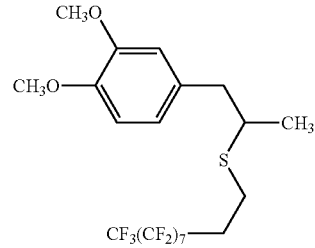

(117B)

A mixture of 1.35 g (7.60 mmol) of 4-allyl-1,2-dimethoxybenzene, 3.65 g (7.60 mmol) of 1H,1H,2H,2H-perfluorodecane-1-thiol and 0.10 g (0.70 mmol) of AIBN [2,2'-azo-bis-(2-methylbutyronitrile)] in 10 ml of dry toluene is heated at 80° C. for 12 hours. Each 2-3 hours, an additional quantity of AIBN (0.10 g) is added. The reaction mixture is evaporated to dryness to give 4.80 g of a yellow wax. The crude material is purified by distillation (175° C./0.07 mbar) to give 3.20 g of an orange solid which is further purified by flash chromatography (hexane/ethyl acetate: 8:1) to give 1.70 g of a mixture of regioisomers 117A and 117B (GC: appr. 88%/12%) as white solid, m.p. 54-60° C. $^1$H NMR: (400 MHz, CDCl$_3$): major regioisomer 117A: δ=6.85-6.80 (m, ArH, 1H); 6.80-6.70 (m, ArH, 2H); 3.90 (s, OCH$_3$, 3H); 3.88 (s, OCH$_3$, 3H); 2.80-2.65 (m, ArCH$_2$CH$_2$CH$_2$S, 4H); 2.58 (t, J=7.2 Hz, SCH$_2$CH$_2$CF$_2$, 2H); 2.50-2.25 (m, SCH$_2$CH$_2$CF$_2$, 2H); 2.00-1.90 (m, ArCH$_2$CH$_2$, 2H). Significant peaks of the minor regioisomer 117B: 3.05-2.80 (m, 2H); 1.29 (d, J=6.4 Hz, CH$_3$, 3H).

EXAMPLE 18

Preparation of Compound 118

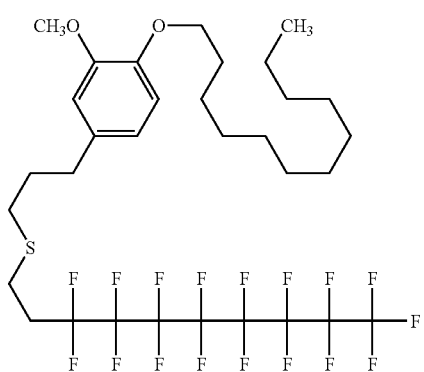

(118)

A mixture of 2.00 g (3.10 mmol) of compound 116A [prepared according to Example 16], 0.80 g (3.10 mmol) of 1-bromododecane and 0.86 g (6.20 g) of pulverized K$_2$CO$_3$ in 20 ml of methyl ethyl ketone is heated under reflux for 12 hours. The reaction mixture is poured into ethyl acetate, washed with 1N NH$_4$Cl, then with brine, dried over Na$_2$SO$_4$, filtered and concentrated using a vacuum rotary evaporator to give 2.55 g of a yellow wax. The crude material is purified by flash chromatography (hexane/ethyl acetate: 9:1) to give 1.30 g of a colourless liquid contaminated by residual amounts of 1-bromodecane which were distilled off to give 0.90 g of the compound 118 as white waxy solid. $^1$H NMR: (300 MHz, CDCl$_3$): major isomer: δ=6.85-6.75 (m, ArH, 1H); 6-75-6.65 (m, ArH, 2H); 4.00 (t, J=6.9 Hz, OCH$_2$CH$_2$, 2H); 3.87 (s, OCH$_3$, 3H); 2.80-2.65 (m, ArCH$_2$CH$_2$CH$_2$S, 4H); 2.57 (t, J=7.2 Hz, SCH$_2$CH$_2$CF$_2$, 2H); 2.50-2.25 (m, SCH$_2$CH$_2$CF$_2$, 2H); 2.00-1.75 (m, ArCH$_2$CH$_2$+OCH$_2$CH$_2$, 4H); 1.55-1.20 (m, CH$_2$, 18H); 1.00-0.80 (m, CH$_3$, 3H).

EXAMPLE 19

Preparation of Compound 119

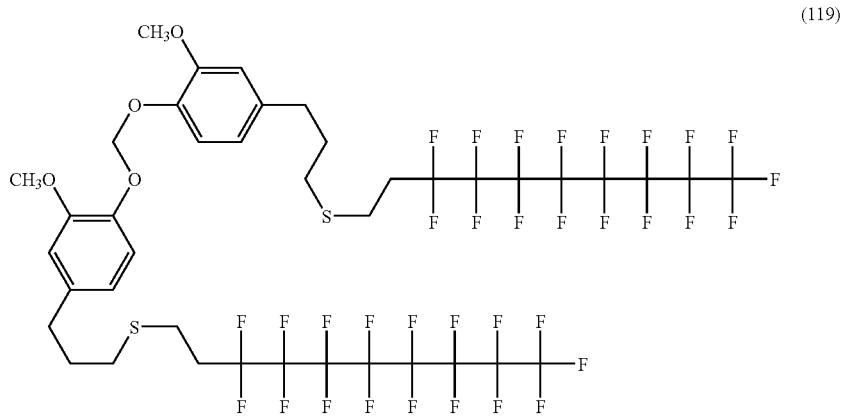

(119)

0.62 g (15.5 mmol) of pulverized sodium hydroxide is added at room temperature to a mixture of 2.00 g (3.10 mmol) of compound 116A [prepared according to Example 16] and 6.32 g (74.4 mmol) of dichloromethane suspended in 9.0 ml of N-methylpyrrolidinone. The reaction mixture is heated at 60° C. for 1 hour. The reaction mixture is poured into ethyl acetate and washed with water. The organic phase is dried over $Na_2SO_4$, filtered and concentrated using a vacuum rotary evaporator to give 2.50 g of a yellow wax, still containing a small amount of the solvent N-methylpyrrolidinone. The crude material is purified by recrystallization from 10 ml of 2-propanol to give 1.00 g of the compound 119 as white solid, m.p. 65-87° C. $^1$H NMR: (300 MHz, $CDCl_3$): major isomer: δ=7.25-7.15 (m, ArH, 2H); 6.80-6.65 (m, ArH, 4H); 5.73 (s, $ArCH_2Ar$, 2H); 3.86 (s, $OCH_3$, 6H); 2.80-2.65 (m, $ArCH_2CH_2CH_2S$, 8H); 2.58 (t, J=7.2 Hz, $SCH_2CH_2CF_2$, 4H); 2.50-2.25 (m, $SCH_2CH_2CF_2$, 4H); 2.00-1.85 (m, $ArCH_2CH_2$, 4H). Significant peaks of the minor isomer: 3.10-2.80 (m); 1.30-1.20 (m, $CH_3$).

EXAMPLE 20

Preparation of Compound 120

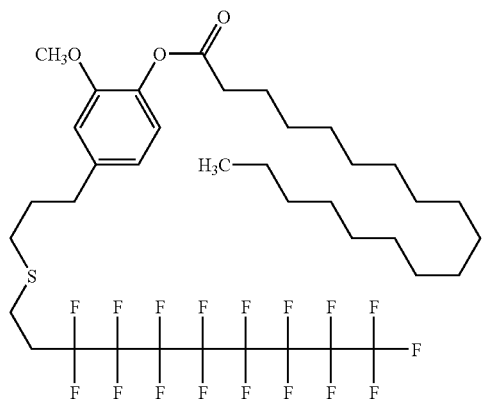

(120)

2.00 g (3.10 mmol) of compound 116A [prepared according to Example 16] and 0.38 g (3.72 mmol) of triethylamine are dissolved in 20 ml of dry tetrahydrofuran. 0.94 g (3.10 mmol) of stearoyl chloride is added to the reaction mixture at room temperature under nitrogen atmosphere. The reaction mixture is stirred at room temperature for 4 hours. Ethyl acetate is added and the organic phase is washed repeatedly with water until pH neutral. The organic phase is dried over magnesium sulfate, filtered and concentrated using a vacuum rotary evaporator to give 2.70 g of a white solid. The crude product is purified by flash chromatography (hexane/ethyl acetate: 7:1) to give 1.90 g of compound 120 as white solid, m.p. 51-53° C. $^1$H NMR: (300 MHz, $CDCl_3$): major isomer: δ=7.00-6.90 (m, ArH, 1H); 6-80-6.70 (m, ArH, 2H); 3.83 (s, $OCH_3$, 3H); 2.85-2.65 (m, $ArCH_2CH_2CH_2S$, 4H); 2.65-2.50 (m, $SCH_2CH_2CF_2$, +$CH_2CO_2$, 4H); 2.50-2.25 (m, $SCH_2CH_2CF_2$, 2H); 2.05-1.85 (m, $ArCH_2CH_2$, 2H); 1.85-1.70 (m, $CH_2CH_2CO_2$, 2H); 1.50-1.20 (m, $CH_2$, 28H); 0.95-0.85 (m, $CH_3$, 3H).

EXAMPLE 21

Preparation of Compound 121

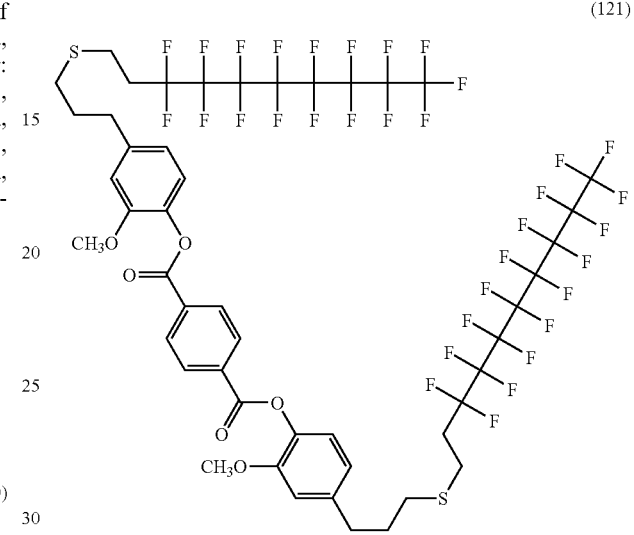

(121)

2.00 g (3.10 mmol) of compound 116A [prepared according to Example 16] and 0.38 g (3.72 mmol) of triethylamine are dissolved in 20 ml of tetrahydrofuran. 0.32 g (1.55 mmol) of terephthaloyl chloride is added to the reaction mixture at room temperature under nitrogen atmosphere. The reaction mixture is stirred at room temperature for 4 hours. The reaction mixture is poured into ethyl acetate and washed with water. The organic phase is dried over magnesium sulfate, filtered and concentrated using a vacuum rotary evaporator to give 2.20 g of a white solid. Recrystallization of the crude product from ethyl acetate/tetrahydrofurane/hexane (1:1:2) gives 0.80 g of the compound 121 as white solid, m.p. 126-150° C. $^1$H NMR: (300 MHz, $CDCl_3$): major isomer: δ=8.35 (s, ArH, 4H); 7.15-7.05 (m, ArH, 2H); 6.90-6.80 (m, ArH, 4H); 3.84 (s, $OCH_3$, 6H); 2.85-2.70 (m, $ArCH_2CH_2CH_2S$, 8H); 2.63 (t, J=7.2 Hz, $SCH_2CH_2CF_2$, 4H); 2.50-2.20 (m, $SCH_2CH_2CF_2$, 4H); 2.05-1.85 (m, $ArCH_2CH_2$, 4H).

EXAMPLE 22

Preparation of a Mixture of Compounds 122a and 122b

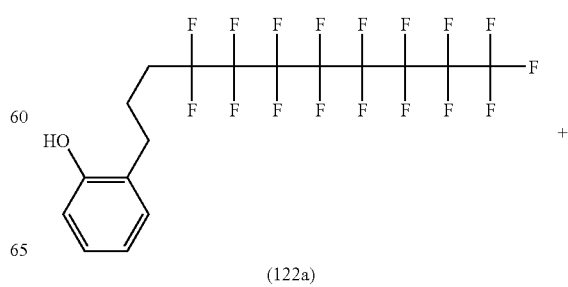

(122a)

+

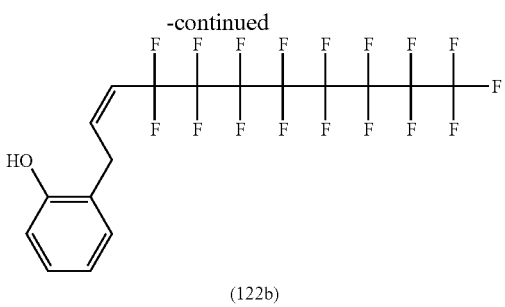

(122b)

25.5 g (42.6 mmol) of the perfluoroalkyl iodide (Telomer-AN, from DuPont) with a homologue distribution and 3.57 g (18.8 mmol) of sodium meta-bisulfite are suspended in a mixture of 1-propanol/water (24 ml/10 ml) under nitrogen atmosphere. The reaction mixture is heated to 60° C. and the pH is adjusted to 6-7 by adding 4 ml of 1M NaOH. 1.12 g (6.82 mmol) of AIBN (2,2'-azo-bis-(2-methylbutyronitrile)) is added, then a solution of 4.58 g (34.1 mmol) of the 2-allylphenol in 1-propanol (7.0 ml) is added dropwise. The reaction is stirred for 12 hours at 60-70° C., then cooled down to room temperature. Water and ethyl acetate are added. The organic phase is washed with water, brine, dried over sodium sulfate, filtered and concentrated using a vacuum rotary evaporator to give 23.9 g of a yellow wax.

The crude mass is then suspended in 120 ml of 1-propanol and 3.00 g (45.8 mmol) of activated Zn is added under nitrogen atmosphere. The reaction mixture is heated under reflux for 12 hours. After cooling to room temperature, the 1-propanol is distilled off. The residue is then poured onto cold aqueous HCl and the aqueous layer is extracted with ethyl acetate. The combined organic layers are washed several times with water, brine, dried over sodium sulfate, filtered and concentrated using a vacuum rotary evaporator to give 19.3 g of a waxy orange solid. The crude product is purified by fractional distillation to give 11.6 g of a mixture of the compound of formula 122a (70%) and compound of the formula 122b (30%) as white waxy solid.

EXAMPLE 23

Preparation of a Mixture of Terephthalic Esters of a Mixture of Compounds 122a and 122b 2.00 g of a mixture of compounds 122a and 122b prepared according to Example 22 and 0.40 g (3.96 mmol) of triethylamine are dissolved in 20 ml of tetrahydrofuran. 0.34 g (1.65 mmol) of terephthaloyl chloride is added to the reaction mixture at room temperature under nitrogen atmosphere. The reaction mixture is stirred at room temperature for 12 hours. The reaction mixture is poured into ethyl acetate, tetrahydrofuran and washed with water. The organic phase is then filtered, dried over magnesium sulfate, filtered and concentrated using a vacuum rotary evaporator to give 2.30 g of a pale yellow wax. The crude product is purified by flash chromatography (hexane/ethyl acetate: 9:1) to give a material from which the residual amounts of educts and impurities are distilled off to give 0.95 g of a mixture of terephthalic esters, white solid, m.p. 79-87° C.

EXAMPLE 24

Water and Oil Repellency in Polypropylene

In order to determine the repellency properties of the compounds of the formula I, they are tested according to the following procedure. The sample preparation is a combination of polypropylene nonwovens and a thermal treatment (e.g. 130° C. for 10 minutes), which increases the migration of the additive to the surface and a proper surface rearrangement of the chemical groups. This extra heat cycle is recommended to melt the compounds of the formula I in order to obtain a homogeneous redistribution over the surface of the substrate. An industrial sample of polypropylene nonwoven, fabric weight: 40 g/m², is dipped into a 1% isopropanol solution of the test compound, simultaneously applying ultrasonic energy for one minute. After that, the sample is dried overnight at room temperature and then two hours at 90° C. in an oven. A part of the sample is afterwards annealed for 10 minutes at 130° C.

The treated nonwoven samples are evaluated in the water repellency test similar to INDA test method 80.8 (99). The wetting behavior of the nonwovens is tested with a series of water/isopropanol mixtures. The observation of the wetting behavior is rated from 0 (water wetting, no repellency) to 10 (optimum water repellency). The results are summarized in Table 1.

The treated nonwoven samples are evaluated in the oil repellency test similar to AATCC test method 118-1997/ISO 14419. This test follows the same concepts of the already described for water repellency test method, but using, as test solvents, a series of hydrocarbons. The observation of the wetting behavior is rated from 0 (no repellency) to 8 (optimum repellency). The results are summarized in Table 2.

TABLE 1

| Example | Compound | Water repellency as received | Water repellency after annealing |
|---|---|---|---|
| 24a | compound 103 | 9 | 8 |
| 24b | compound 106 | 3 | 9 |
| 24c | compound 107 | 9 | 9 |
| 24d | compound 112 | 6 | 9 |
| 24e | compound 115 | 9 | 10 |
| 24f | compound 119 | 9 | 9 |
| 24g | compound 121 | 7 | 9 |
| 24h | Example 23 | 9 | 9 |

TABLE 2

| Example | Compound | Oil repellency as received | Oil repellency after annealing |
|---|---|---|---|
| 24i | compound 105 | 8 | 8 |
| 24j | compound 107 | 5 | 6 |
| 24k | compound 115 | 7 | 5 |

EXAMPLE 25

Water and Oil Repellency in Polypropylene Nonwoven Fibers

Compounding: Samples of the compounds of formula I are heated in an oven at 70° C. until they are completely liquefied. The liquid is added at 10-20 ml/min to a twin-screw extrusion of polypropylene pellets via a heated graduated cylinder using a Leistritz MIC 27/GL-32D twin-screw extruder. The extruder zones are 150°-195° C. with the main screw at 500 RPM and the PP feeder at 200-250 RPM. The molten polymer and additive exit via a two orifice round die. The molten material is immediately cooled and solidified in a cold-water trough. The solidified strand is fed into a Conair/Jetro 304 Pelletizer. The polypropylene used for the spunbond processing is PP 3155 from ExxonMobil (melt flow rate 36 g/10 min)

and PP 3546 from ExxonMobil (melt flow rate 1200 g/10 min) for the meltblown processing.

Alternatively, the compounds of formula I are made into masterbatches by those skilled in the technique. The masterbatch at the desired level is then tumble mixed with the appropriate polypropylene for making spunbond and meltblown nonwovens.

Tumble Mixing The concentrate pellets are let down with additional polypropylene pellets and are mixed with a Marion SPS 1224 mixer, resulting in a desired additive concentration by weight.

Meltblown Process Meltblown polypropylene fabrics are prepared from the tumble-mixed additives pellets prepared as above using a custom-built 6-inch Melt Blowing Pilot Line under the following conditions: Extruder temperature of 175-240° C. Die and air temperature of 240° C. Throughput 0.479 g/h/m (22 kg/hour/meter). Collector belt speed is adjusted to produce a nonwoven with a basis weight of 40-45 gsm.

The produced nonwoven samples are evaluated on their water/alcohol repellency behaviour similar to INDA standards (International Nonwoven and Disposables Association) and their oil repellency behaviour similar to AATCC standards. The results are summarized in Tables 3 and 4.

TABLE 3

| Example | Compound | Water repellency as received | Water repellency after annealing |
|---|---|---|---|
| 25a | 1.0% of compound 107 | 8 | 9 |
| 25b | 1.0% of compound 119 | 9 | 9 |

TABLE 4

| Example | Compound | Oil repellency as received | Oil repellency after annealing |
|---|---|---|---|
| 25c | 1.0% of compound 107 | 2 | 5 |
| 25d | 1.0% of compound 119 | 3 | 5 |

What is claimed is:

1. A composition comprising
a) a synthetic polymer which is susceptible to oxidative, thermal or light-induced degradation, and
b) at least one compound of formula I

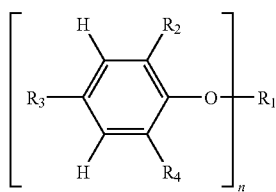
(I)

wherein, when n is 1,
$R_1$ is hydrogen, $C_1$-$C_{25}$alkyl, $C_2$-$C_{25}$alkenyl, —CO—$R_5$, —CH($R_{10}$)CO—$R_5$, —C($R_{10}$)$_2$CO—$R_5$, —CO—N($R_6$)—$R_7$, —CH($R_{10}$)CO—N($R_6$)—$R_7$, —C($R_{10}$)$_2$CO—N($R_6$)—$R_7$, —CH($R_{10}$)COO$R_5$ or —C($R_{10}$)$_2$CO—O$R_5$;

when n is 2,
$R_1$ is unsubstituted or $C_1$-$C_4$alkyl, benzyl or phenyl substituted $C_1$-$C_{24}$alkylene; oxygen or sulfur interrupted $C_2$-$C_{24}$alkylene; —CO—$R_8$—CO—, —CH($R_{10}$)CO—$R_8$—CO—CH($R_{10}$)—, —C($R_{10}$)$_2$CO—$R_8$—CO—C($R_{10}$)$_2$—, —CO—N($R_6$)—$R_9$—N($R_6$)—CO—, —CH($R_{10}$)CO—N($R_6$)—$R_9$—N($R_6$)—CO—CH($R_{10}$)—, —C($R_{10}$)$_2$CO—N($R_6$)—$R_9$—N($R_6$)—CO—C($R_{10}$)$_2$—, —CH($R_{10}$)CO—O—$R_9$—O—CO—CH($R_{10}$)— or —C($R_{10}$)$_2$CO—O—$R_9$—O—CO—C($R_{10}$)$_2$—;

when n is 3,
$R_1$ is

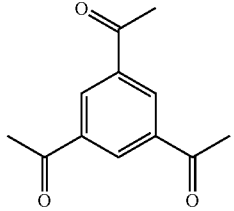

$R_2$, $R_3$ and $R_4$ independently of each other are hydrogen, $C_2$-$C_{25}$alkenyl, $C_1$-$C_{25}$alkoxy, —CH$_2$—CH(CH$_3$)—S(O)$_p$—$R_{12}$, —CH$_2$—CH$_2$—CH$_2$—S(O)$_p$—$R_{12}$, —CH$_2$—CH($R_{11}$)—CH$_2$—$R_{12}$, —CH$_2$—CH=CH—$R_{12}$,

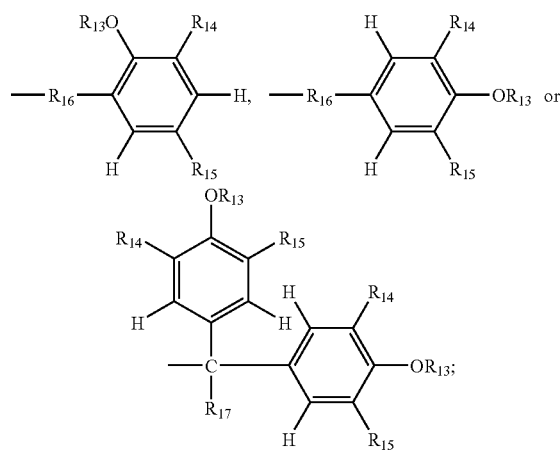

with the proviso that at least one of the radicals $R_2$, $R_3$ or $R_4$ is —CH$_2$—CH(CH$_3$)—S(O)$_p$—$R_{12}$, —CH$_2$—CH$_2$—CH$_2$—S(O)$_p$—$R_{12}$, —CH$_2$—CH($R_{11}$)—CH$_2$—$R_{12}$ or —CH$_2$—CH=CH—$R_{12}$;

$R_5$ is $C_1$-$C_{25}$alkyl, $C_2$-$C_{25}$alkenyl, unsubstituted or $C_1$-$C_4$alkyl or halogen substituted phenyl; or $C_7$-$C_{12}$-phenylalkyl, $R_6$ is hydrogen or $C_1$-$C_4$alkyl, $R_7$ is hydrogen, $C_1$-$C_{25}$alkyl, unsubstituted or $C_1$-$C_4$alkyl or halogen substituted phenyl;

$R_8$ is phenylene, nitro substituted phenylene; unsubstituted or $C_1$-$C_4$alkyl, benzyl or phenyl substituted $C_1$-$C_{24}$alkylene; oxygen or sulfur interrupted $C_2$-$C_{24}$alkylene;

$R_9$ is a direct bond; unsubstituted or $C_1$-$C_4$alkyl, benzyl or phenyl substituted $C_2$-$C_{24}$alkylene; oxygen or sulfur interrupted $C_2$-$C_{24}$alkylene; or

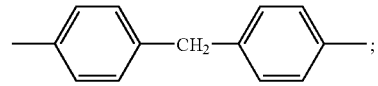

$R_{10}$ is hydrogen or $C_1$-$C_8$alkyl, $R_{11}$ is hydrogen or halogen, $R_{12}$ is a monovalent perfluorinated alkyl or alkenyl, linear or branched organic radical having four to twenty fully fluorinated carbon atoms; or —$CH_2CH_2(CF_2)_mCF_3$, $R_{13}$ is hydrogen, $C_1$-$C_{25}$alkyl, $C_2$-$C_{25}$alkenyl, —CO—$R_5$, —CO—N($R_6$)—$R_7$ or —$CH_2$—CO—N($R_6$)—$R_7$, $R_{14}$ is hydrogen, $C_1$-$C_{25}$alkyl, $C_2$-$C_{25}$alkenyl, $C_1$-$C_{25}$alkoxy, —$CH_2$—CH($CH_3$)—S(O)$_p$—$R_{12}$, —$CH_2$—$CH_2$—$CH_2$—S(O)$_p$—$R_{12}$, —$CH_2$—CH($R_{11}$)—$CH_2$—$R_{12}$, or —$CH_2$—CH=CH—$R_{12}$, $R_{15}$ is hydrogen, $C_1$-$C_{25}$alkyl, $C_2$-$C_{25}$alkenyl, $C_1$-$C_{25}$alkoxy, —$CH_2$—CH($CH_3$)—S(O)$_p$—$R_{12}$, —$CH_2$—$CH_2$—$CH_2$—S(O)$_p$—$R_{12}$, —$CH_2$—CH($R_{11}$)—$CH_2$—$R_{12}$ or —$CH_2$—CH=CH—$R_{12}$, $R_{16}$ is unsubstituted or $C_1$-$C_4$alkyl substituted methylene, —S—, —S(O)—, —S(O)$_2$— or —CO—;

$R_{17}$ is $C_1$-$C_4$alkyl, m is 3 to 12, n is 1, 2 or 3, and p is 0, 1 or 2.

2. A composition according to claim 1, wherein, when n is 1, $R_1$ is hydrogen, $C_1$-$C_{25}$alkyl, $C_2$-$C_{25}$alkenyl, —CO—$R_5$, —CH($R_{10}$)CO—$R_5$, —C($R_{10}$)$_2$CO—$R_5$, —CO—N($R_6$)—$R_7$, —CH($R_{10}$)CO—N($R_6$)—$R_7$, —C($R_{10}$)$_2$CO—N($R_6$)—$R_7$, —CH($R_{10}$)COOR$_5$ or —C($R_{10}$)$_2$CO—OR$_5$;

when n is 2, $R_1$ is unsubstituted or $C_1$-$C_4$alkyl, benzyl or phenyl substituted $C_1$-$C_{24}$alkylene; oxygen or sulfur interrupted $C_2$-$C_{24}$alkylene; —CO—$R_8$—CO—, —CH($R_{10}$)CO—$R_8$—CO—CH($R_{10}$)—, —C($R_{10}$)$_2$CO—$R_8$—CO—C($R_{10}$)$_2$—, —CO—N($R_6$)—$R_9$—N($R_6$)—CO—, —CH($R_{10}$)CO—N($R_6$)—$R_9$—N($R_6$)—CO—CH($R_{10}$)—, —C($R_{10}$)$_2$CO—N($R_6$)—$R_9$—N($R_6$)—CO—C($R_{10}$)$_2$—, —CH($R_{10}$)CO—O—$R_9$—O—CO—CH($R_{10}$)— or —C($R_{10}$)$_2$CO—O—$R_9$—O—CO—C($R_{10}$)$_2$—;

when n is 3, $R_1$ is

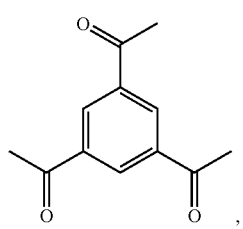

$R_2$, $R_3$ and $R_4$ independently of each other are hydrogen, $C_2$-$C_{25}$alkenyl, $C_1$-$C_{25}$alkoxy, —$CH_2$—CH($CH_3$)—S(O)$_p$—$R_{12}$, —$CH_2$—$CH_2$—$CH_2$—S(O)$_p$—$R_{12}$, —$CH_2$—CH($R_{11}$)—$CH_2$—$R_{12}$,

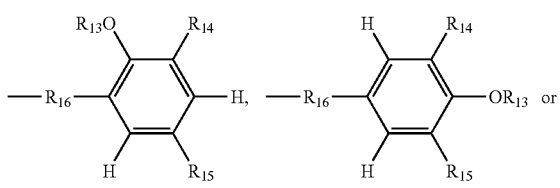

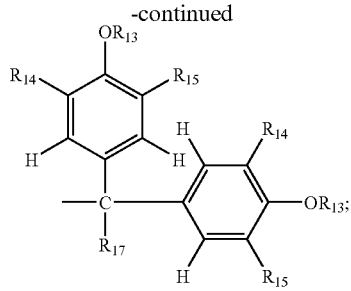

with the proviso that at least one of the radicals $R_2$, $R_3$ or $R_4$ is —$CH_2$—CH($CH_3$)—S(O)$_p$—$R_{12}$, —$CH_2$—$CH_2$—$CH_2$—S(O)$_p$—$R_{12}$ or —$CH_2$—CH($R_{11}$)—$CH_2$—$R_{12}$;

$R_5$ is $C_1$-$C_{25}$alkyl, $C_2$-$C_{25}$alkenyl, unsubstituted or $C_1$-$C_4$alkyl or halogen substituted phenyl; or $C_7$-$C_{12}$phenylalkyl, $R_6$ is hydrogen or $C_1$-$C_4$alkyl, $R_7$ is hydrogen, $C_1$-$C_{25}$alkyl, unsubstituted or $C_1$-$C_4$alkyl or halogen substituted phenyl;

$R_8$ is phenylene, nitro substituted phenylene; unsubstituted or $C_1$-$C_4$alkyl, benzyl or phenyl substituted $C_1$-$C_{24}$alkylene; oxygen or sulfur interrupted $C_2$-$C_{24}$alkylene;

$R_9$ is a direct bond; unsubstituted or $C_1$-$C_4$alkyl, benzyl or phenyl substituted $C_2$-$C_{24}$alkylene; oxygen or sulfur interrupted $C_2$-$C_{24}$alkylene; or

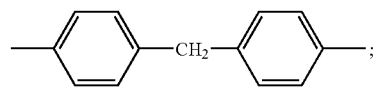

$R_{10}$ is hydrogen or $C_1$-$C_3$alkyl, $R_{11}$ is hydrogen or halogen, $R_{12}$ is a monovalent perfluorinated alkyl or alkenyl, linear or branched organic radical having four to twenty fully fluorinated carbon atoms, $R_{13}$ is hydrogen, $C_1$-$C_{25}$alkyl, $C_2$-$C_{25}$alkenyl, —CO—$R_5$, —CO—N($R_6$)—$R_7$ or —$CH_2$—CO—N($R_6$)—$R_7$, $R_{14}$ is hydrogen, $C_1$-$C_{25}$alkyl, $C_2$-$C_{25}$alkenyl, $C_1$-$C_{25}$alkoxy, —$CH_2$—CH($CH_3$)—S(O)$_p$—$R_{12}$, —$CH_2$—$CH_2$—$CH_2$—S(O)$_p$—$R_{12}$ or —$CH_2$—CH($R_{11}$)—$CH_2$—$R_{12}$, $R_{15}$ is hydrogen, $C_1$-$C_{25}$alkyl, $C_2$-$C_{25}$alkenyl, $C_1$-$C_{25}$alkoxy, —$CH_2$—CH($CH_3$)—S(O)$_p$—$R_{12}$, —$CH_2$—$CH_2$—$CH_2$—S(O)$_p$—$R_{12}$ or —$CH_2$—CH($R_{11}$)—$CH_2$—$R_{12}$, $R_{16}$ is unsubstituted or $C_1$-$C_4$alkyl substituted methylene, —S—, —S(O)—, —S(O)$_2$— or —CO—;

$R_{17}$ is $C_1$-$C_4$alkyl, n is 1, 2 or 3, and p is 0, 1 or 2.

3. A composition according to claim 1, wherein, when n is 1, $R_1$ is hydrogen, $C_1$-$C_{18}$alkyl, $C_2$-$C_{18}$alkenyl, —CO—$R_5$, —CO—N($R_6$)—$R_7$ or —$CH_2$—CO—N($R_6$)—$R_7$;

when n is 2, $R_1$ is unsubstituted or $C_1$-$C_4$alkyl, benzyl or phenyl substituted $C_1$-$C_{18}$alkylene; oxygen or sulfur interrupted $C_2$-$C_{18}$alkylene; —CO—$R_8$—CO—, —CO—N($R_6$)—$R_9$—N($R_6$)—CO— or —CH($R_{10}$)—CO—N($R_6$)—$R_9$—N($R_6$)—CO—CH($R_{10}$)—;

when n is 3, $R_1$ is

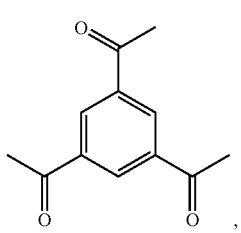

R$_2$, R$_3$ and R$_4$ independently of each other are hydrogen, C$_2$-C$_{18}$alkenyl, C$_1$-C$_{18}$alkoxy, —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$, —CH$_2$—CH=CH—R$_{12}$,

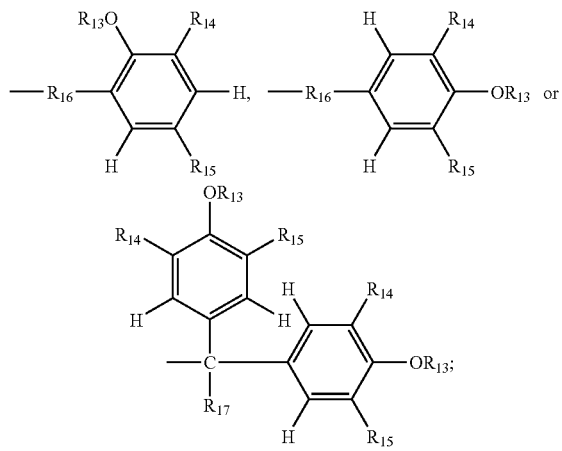

with the proviso that at least one of the radicals R$_2$, R$_3$ or R$_4$ is —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$ or —CH$_2$—CH=CH—R$_{12}$;

R$_5$ is C$_1$-C$_{18}$alkyl, C$_2$-C$_{18}$alkenyl, unsubstituted or C$_1$-C$_4$alkyl or halogen substituted phenyl; or C$_7$-C$_{12}$-phenylalkyl, R$_6$ is hydrogen or C$_1$-C$_4$alkyl, R$_7$ is hydrogen, C$_1$-C$_{18}$alkyl, unsubstituted or C$_1$-C$_4$alkyl or halogen substituted phenyl;

R$_8$ is phenylene, unsubstituted or C$_1$-C$_4$alkyl, benzyl or phenyl substituted C$_1$-C$_{24}$alkylene; oxygen or sulfur interrupted C$_2$-C$_{24}$alkylene;

R$_9$ is a direct bond, unsubstituted or C$_1$-C$_4$alkyl, benzyl or phenyl substituted C$_2$-C$_{18}$alkylene; or

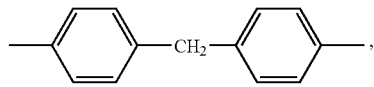

R$_{10}$ is hydrogen or C$_1$-C$_3$alkyl,

R$_{11}$ is hydrogen or halogen,

R$_{12}$ is a monovalent perfluorinated alkyl or alkenyl, linear or branched organic radical having four to twenty fully fluorinated carbon atoms, R$_{13}$ is hydrogen, C$_1$-C$_{18}$alkyl, C$_2$-C$_{18}$alkenyl, —CO—R$_5$, —CO—N(R$_6$)—R$_7$ or —CH$_2$—CO—N(R$_6$)—R$_7$, R$_{14}$ is hydrogen, C$_1$-C$_{18}$alkyl, C$_2$-C$_{18}$alkenyl, C$_1$-C$_{18}$alkoxy, —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$ or —CH$_2$—CH=CH—R$_{12}$, R$_{15}$ is hydrogen, C$_1$-C$_{18}$alkyl, C$_2$-C$_{18}$alkenyl, C$_1$-C$_{18}$alkoxy, —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$ or —CH$_2$—CH=CH—R$_{12}$, R$_{16}$ is unsubstituted or C$_1$-C$_4$alkyl substituted methylene, —S—, —S(O)—, —S(O)$_2$— or —CO—;

R$_{17}$ is C$_1$-C$_4$alkyl, n is 1, 2 or 3, and p is 0, 1 or 2.

4. A composition according to claim 1, wherein R$_{12}$ is saturated and contains 4-15 carbon atoms, is fully fluorinated and contains at least one terminal perfluoromethyl group; or is —CH$_2$CH$_2$(CF$_2$)$_m$CF$_3$ where m is 3 to 12.

5. A composition according to claim 1, wherein

R$_2$, R$_3$ and R$_4$ independently of each other are hydrogen, C$_1$-C$_4$alkoxy, —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$, —CH$_2$—CH=CH—R$_{12}$ or

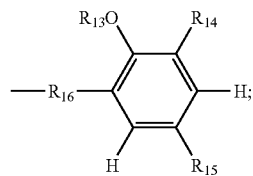

with the proviso that at least one of the radicals R$_2$, R$_3$ or R$_4$ is —CH$_2$—CH(CH$_3$)—S(O)—R$_{12}$, —CH$_2$—CH$_2$—CH$_2$—S(O)$_p$—R$_{12}$, —CH$_2$—CH(R$_{11}$)—CH$_2$—R$_{12}$ or —CH$_2$—CH=CH—R$_{12}$;

R$_{11}$ is hydrogen or halogen,

R$_{12}$ is a monovalent perfluorinated alkyl or alkenyl, linear or branched organic radical having four to twenty fully fluorinated carbon atoms, R$_{13}$ is hydrogen, C$_1$-C$_{18}$alkyl, C$_2$-C$_{18}$alkenyl or acetyl, R$_{14}$ is hydrogen, C$_1$-C$_{18}$alkyl, C$_2$-C$_{18}$alkenyl, C$_1$-C$_{18}$alkoxy, —CH$_2$—CH(CH$_3$)—S(O)$_p$—R$_{12}$, —CH$_2$—CH$_2$—CH$_2$—S(O)$_p$—R$_{12}$, —CH$_2$—CH(R$_{11}$)—CH$_2$—R$_{12}$ or —CH$_2$—CH=CH—R$_{12}$, R$_{15}$ is hydrogen, C$_1$-C$_{18}$alkyl, C$_2$-C$_{18}$alkenyl, C$_1$-C$_{18}$alkoxy, —CH$_2$—CH(CH$_3$)—S(O)$_p$—R$_{12}$, —CH$_2$—CH$_2$—CH$_2$—S(O)—R$_{12}$, —CH$_2$—CH(R$_{11}$)—CH$_2$—R$_{12}$ or —CH$_2$—CH=CH—R$_{12}$, R$_{16}$ is unsubstituted or C$_1$-C$_4$alkyl substituted methylene, —S—, —S(O)—, —S(O)$_2$— or —CO—; and p is 0, 1 or 2.

6. A composition according to claim 1, wherein, when n is 1,

R$_1$ is hydrogen, C$_1$-C$_{18}$alkyl, —CO—R$_5$, —CO—N(R$_6$)—R$_7$ or —CH$_2$—CO—N(R$_6$)—R$_7$;

when n is 2,

R$_1$ is unsubstituted or C$_1$-C$_4$alkyl substituted C$_1$-C$_8$alkylene; —CO—R$_8$—CO—, —CO—N(R$_6$)—R$_9$—N(R$_6$)—CO— or —CH(R$_{10}$)—CO—N(R$_8$)—R$_9$—N(R$_8$)—CO—CH(R$_{10}$)—, when n is 3,
R₁ is

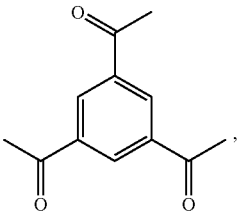

R₂, R₃ and R₄ independently of each other are hydrogen, $C_1$-$C_8$alkoxy, —CH₂—CH(CH₃)—S(O)$_p$—R₁₂, —CH₂—CH₂—CH₂—S(O)$_p$—R₁₂, —CH₂—CH(R₁₁)—CH₂—R₁₂, —CH₂—CH=CH—R₁₂,

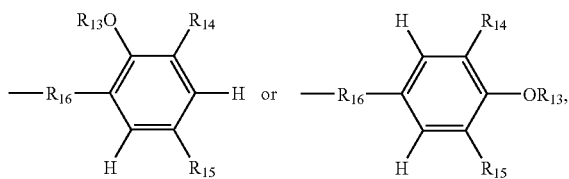

with the proviso that at least one of the radicals R₂, R₃ or R₄ is —CH₂—CH(CH₃)—S(O)$_p$—R₁₂, —CH₂—CH₂—CH₂—S(O)$_p$—R₁₂, —CH₂—CH(R₁₁)—CH₂—R₁₂ or —CH₂—CH=CH—R₁₂;
R₅ is $C_1$-$C_{18}$alkyl, unsubstituted or $C_1$-$C_4$alkyl substituted phenyl; or $C_7$-$C_{12}$phenylalkyl,
R₆ is hydrogen or $C_1$-$C_4$alkyl,
R₇ is hydrogen, $C_1$-$C_8$alkyl, unsubstituted or $C_1$-$C_4$alkyl substituted phenyl;
R₈ is phenylene, unsubstituted or $C_1$-$C_4$alkyl substituted $C_1$-$C_{18}$alkylene;
R₉ is unsubstituted or $C_1$-$C_4$alkyl substituted $C_2$-$C_{18}$alkylene; or

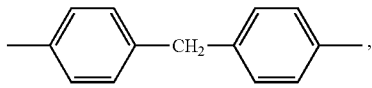

R₁₀ is hydrogen or $C_1$-$C_8$alkyl,
R₁₁ is hydrogen, fluoro, chloro or bromo,
R₁₂ is saturated and contains 4-15 carbon atoms, is fully fluorinated and contains at least one terminal perfluoromethyl group,
R₁₃ is hydrogen, $C_1$-$C_{12}$alkyl, —CO—R₅, —CO—N(R₆)—R₇ or —CH₂—CO—N(R₆)—R₇,
R₁₄ is hydrogen, $C_1$-$C_{12}$alkyl, $C_1$-$C_{12}$alkoxy, —CH₂—CH(CH₃)—S(O)$_p$—R₁₂, —CH₂—CH₂—CH₂—S(O)$_p$—R₁₂, —CH₂—CH(R₁₁)—CH₂—R₁₂ or —CH₂—CH=CH—R₁₂,
R₁₅ is $C_1$-$C_{18}$alkyl, $C_1$-$C_{12}$alkoxy, —CH₂—CH(CH₃)—S(O)$_p$—R₁₂, —CH₂—CH₂—CH₂—S(O)$_p$—R₁₂, —CH₂—CH(R₁₁)—CH₂—R₁₂ or —CH₂—CH=CH—R₁₂,
R₁₆ is unsubstituted or $C_1$-$C_4$alkyl substituted methylene;
n is 1, 2 or 3, and
p is 0.

7. A composition according to claim 1, wherein,
when n is 1,
R₁ is hydrogen, $C_1$-$C_{18}$alkyl, —CO—R₅, —CO—N(R₈)—R₇ or —CH₂—CO—N(R₆)—R₇, when n is 2,
R₁ is $C_1$-$C_8$alkylene, —CO—R₈—CO—, —CO—N(R₆)—R₉—N(R₆)—CO— or —CH(R₁₀)—CO—N(R₈)—R₉—N(R₈)—CO—CH(R₁₀)—,
when n is 3,
R₁ is

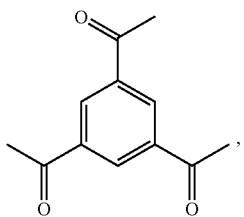

R₂, R₃ and R₄ independently of each other are hydrogen, $C_1$-$C_8$alkoxy, —CH₂—CH(CH₃)—S(O)$_p$—R₁₂, —CH₂—CH₂—CH₂—S(O)$_p$—R₁₂, —CH₂—CH(R₁₁)—CH₂—R₁₂, —CH₂—CH=CH—R₁₂,

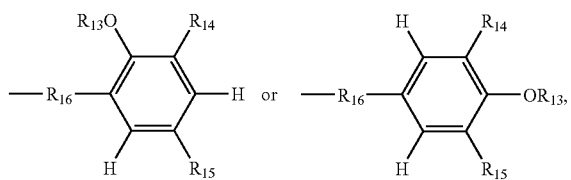

with the proviso that at least one of the radicals R₂, R₃ or R₄ is —CH₂—CH(CH₃)—S(O)$_p$—R₁₂, —CH₂—CH₂—CH₂—S(O)$_p$—R₁₂, —CH₂—CH(R₁₁)—CH₂—R₁₂ or —CH₂—CH=CH—R₁₂;
R₅ is $C_1$-$C_{18}$alkyl, unsubstituted or $C_1$-$C_4$alkyl substituted phenyl; or benzyl,
R₆ is hydrogen,
R₇ is hydrogen, $C_1$-$C_8$alkyl, unsubstituted or $C_1$-$C_4$alkyl substituted phenyl;
R₈ is phenylene or $C_1$-$C_{18}$alkylene,
R₉ is $C_2$-$C_{18}$alkylene or

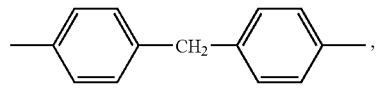

R₁₀ is $C_1$-$C_4$alkyl,
R₁₁ is hydrogen or fluoro, choro or bromo,
R₁₂ is —(CF₂)$_m$CF₃ or —CH₂CH₂(CF₂)$_m$CF₃,
R₁₃ is hydrogen or —CO—R₅,
R₁₄ is hydrogen or $C_1$-$C_3$alkyl or $C_1$-$C_8$alkoxy,
R₁₅ is —CH₂—CH(CH₃)—S(O)$_p$—R₁₂, —CH₂—CH₂—CH₂—S(O)$_p$—R₁₂ or —CH₂—CH(R₁₁)—CH₂—R₁₂,
R₁₆ is methylene,
m is 3 to 12,
n is 1, 2 or 3, and
p is 0.

8. A composition according to claim 1, wherein,
when n is 1,
R₁ is hydrogen, $C_1$-$C_{12}$alkyl, —CO—R₅, —CO—N(R₆)—R₇ or —CH₂—CO—N(R₆)—R₇;
when n is 2,
R₁ is methylene, —CO—R₈—CO— or —CH(R₁₀)—CO—N(R₈)—R₉—N(R₈)—CO—CH(R₁₀)—;

when n is 3,
$R_1$ is

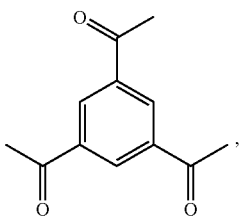, $R_2$, $R_3$ and $R_4$ independently of each other are hydrogen, $C_1$-$C_4$alkoxy, —$CH_2$—$CH(CH_3)$—$S(O)_p$—$R_{12}$, —$CH_2$—$CH_2$—$CH_2$—$S(O)_p$—$R_{12}$, —$CH_2$—$CH(R_{11})$—$CH_2$—$R_{12}$, —$CH_2$—$CH$=$CH$—$R_{12}$ or

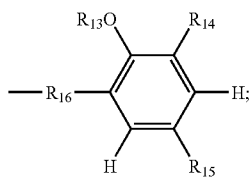

with the proviso that at least one of the radicals $R_2$, $R_3$ or $R_4$ is —$CH_2$—$CH(CH_3)$—$S(O)_p$—$R_{12}$, —$CH_2$—$CH_2$—$CH_2$—$S(O)_p$—$R_{12}$, —$CH_2$—$CH(R_{11})$—$CH_2$—$R_{12}$ or —$CH_2$—$CH$=$CH$—$R_{12}$;

$R_5$ is $C_1$-$C_{18}$alkyl,
$R_6$ is hydrogen,
$R_7$ is hydrogen, $C_1$-$C_6$alkyl, unsubstituted or $C_1$-$C_4$alkyl substituted phenyl;
$R_8$ is phenylene or

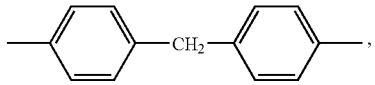, $R_9$ is ethylene,
$R_{10}$ is methyl,
$R_{11}$ is hydrogen,
$R_{12}$ is —$(CF_2)_mCF_3$ or —$CH_2CH_2(CF_2)_mCF_3$,
$R_{13}$ is hydrogen or acetyl,
$R_{14}$ is $C_1$-$C_4$alkyl,
$R_{15}$ is —$CH_2$—$CH(CH_3)$—$S(O)_p$—$R_{12}$, —$CH_2$—$CH_2$—$CH_2$—$S(O)_p$—$R_{12}$ or —$CH_2$—$CH(R_{11})$—$CH_2$—$R_{12}$,
$R_{16}$ is methylene,
m is 3 to 12,
n is 1, 2 or 3, and
p is 0.

9. A composition according to claim 1 wherein component (a) is a fiber or nonwoven.

10. A composition according to claim 1 wherein component (b) is present in an amount of from 0.01 to 10%, based on the weight of component (a).

11. A composition according to claim 1, comprising in addition, besides components (a) and (b), further additives.

12. A composition according to claim 11, comprising as further additives phenolic antioxidants, light-stabilizers and/or processing stabilizers.

13. A composition according to claim 1 where component a) is polypropylene or polyethylene.

14. A process for reducing the surface energy of a synthetic polymer, which process comprises treating a synthetic polymer with at least a compound of formula I

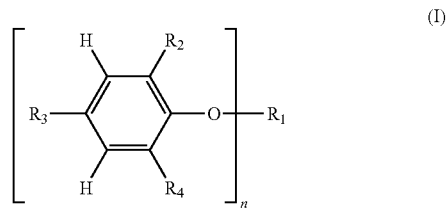

wherein, when n is 1,
$R_1$ is hydrogen, $C_1$-$C_{25}$alkyl, $C_2$-$C_{25}$alkenyl, —CO—$R_5$, —$CH(R_{10})CO$—$R_5$, —$C(R_{10})_2CO$—$R_5$, —CO—N($R_6$)—$R_7$, —$CH(R_{10})CO$—N($R_6$)—$R_7$, —$C(R_{10})_2CO$—N($R_6$)—$R_7$, $CH(R_{10})$ $COOR_5$ or —$C(R_{10})_2$CO—$OR_5$;

when n is 2,
$R_1$ is unsubstituted or $C_1$-$C_4$alkyl, benzyl or phenyl substituted $C_1$-$C_{24}$alkylene; oxygen or sulfur interrupted $C_2$-$C_{24}$alkylene; —CO—$R_8$—CO—, $CH(R_{10})CO$—$R_8$—CO—$CH(R_{10})$—, —$C(R_{10})_2CO$—$R_8$—CO—$C(R_{10})_2$—, —CO—N($R_6$)—$R_9$—N($R_6$)—CO—, —$CH(R_{10})CO$—N($R_6$)—$R_9$—N($R_6$)—CO—$CH(R_{10})$—, —$C(R_{10})_2CO$—N($R_6$)—$R_9$—N($R_6$)—CO—$C(R_{10})_2$—, —$CH(R_{10})CO$—O—$R_9$—O—CO—$CH(R_{10})$— or —$C(R_{10})_2CO$—O—$R_9$—O—CO—$C(R_{10})_2$—;

when n is 3,
$R_1$ is

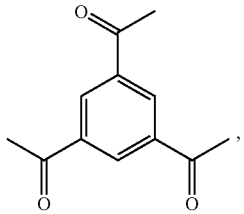, $R_2$, $R_3$ and $R_4$ independently of each other are hydrogen, $C_2$-$C_{25}$alkenyl, $C_1$-$C_{25}$alkoxy, $CH_2$—$CH(CH_3)$—$S(O)_p$—$R_{12}$, —$CH_2$—$CH_2$—$CH_2$—$S(O)_p$—$R_{12}$, —$CH_2$—$CH(R_{11})$—$CH_2$—$R_{12}$, —$CH_2$—$CH$=$CH$—$R_{12}$,

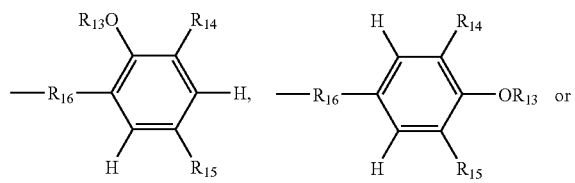

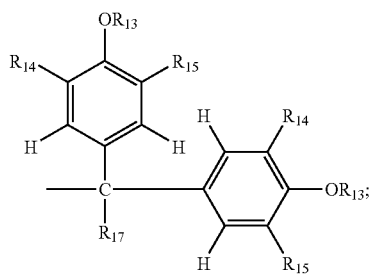

with the proviso that at least one of the radicals $R_2$, $R_3$ or $R_4$ is —$CH_2$—$CH(CH_3)$—$S(O)_p$—$R_{12}$, —$CH_2$—$CH_2$—$CH_2$—$S(O)_p$—$R_{12}$, —$CH_2$—$CH(R_{11})$—$CH_2$—$R_{12}$ or —$CH_2$—$CH$=$CH$—$R_{12}$;

$R_5$ is $C_1$-$C_{25}$alkyl, $C_2$-$C_{25}$alkenyl, unsubstituted or $C_1$-$C_4$alkyl or halogen substituted phenyl; or $C_7$-$C_{12}$phenylalkyl, $R_6$ is hydrogen or $C_1$-$C_4$alkyl, $R_7$ is hydrogen, $C_1$-$C_{25}$alkyl, unsubstituted or $C_1$-$C_4$alkyl or halogen substituted phenyl;

$R_8$ is phenylene, nitro substituted phenylene; unsubstituted or $C_1$-$C_4$alkyl, benzyl or phenyl substituted $C_1$-$C_{24}$alkylene; oxygen or sulfur interrupted $C_2$-$C_{24}$alkylene;

$R_9$ is a direct bond; unsubstituted or $C_1$-$C_4$alkyl, benzyl or phenyl substituted $C_2$-$C_{24}$alkylene; oxygen or sulfur interrupted $C_2$-$C_{24}$alkylene; or

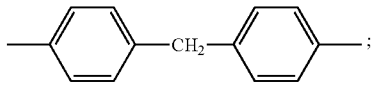;

$R_{10}$ is hydrogen or $C_1$-$C_8$alkyl, $R_{11}$ is hydrogen or halogen, $R_{12}$ is a monovalent perfluorinated alkyl or alkenyl, linear or branched or organic radical having four to twenty fully fluorinated carbon atoms; or —$CH_2CH_2(CF_2)_m$$CF_3$, $R_{13}$ is hydrogen, $C_1$-$C_{25}$alkyl, $C_2$-$C_{25}$alkenyl, —CO—$R_5$—, —CO—N($R_6$)—$R_7$ or —$CH_2$—CO—N($R_6$)—$R_7$, $R_{14}$ is hydrogen, $C_1$-$C_{25}$alkyl, $C_2$-$C_{25}$alkenyl, $C_1$-$C_{25}$alkoxy, —$CH_2$—$CH(CH_3)$—$S(O)_p$—$R_{12}$, —$CH_2$—$CH_2$—$CH_2$—$SO_p$—$R_{12}$, —$CH_2$—$CH(R_{11})$—$CH_2$—$R_{12}$ or —$CH_2$—$CH$=$CH$—$R_{12}$, $R_{15}$ is hydrogen, $C_1$-$C_{25}$alkyl, $C_2$-$C_{25}$alkenyl, $C_1$-$C_{25}$alkoxy, —$CH_2$—$CH(CH_3)$—$S(O)_p$—$R_{12}$, —$CH_2$—$CH_2$—$CH_2$—$SO_p$—$R_{12}$, —$CH_2$—$CH(R_{11})$—$CH_2$—$R_{12}$ or —$CH_2$—$CH$=$CH$—$R_{12}$, $R_{16}$ is unsubstituted or $C_1$-$C_4$alkyl substituted methylene, —S—, —S(O)—, —$S(O)_2$— or —CO—;

$R_{17}$ is $C_1$-$C_4$alkyl, m is 3 to 12, n is 1, 2 or 3, and p is 0, 1 or 2.

* * * * *